(12) United States Patent
Addison et al.

(10) Patent No.: US 12,426,859 B2
(45) Date of Patent: Sep. 30, 2025

(54) BIOPSY SYSTEM AND COUPLER DEVICE FOR USE THEREWITH

(71) Applicant: BARD PERIPHERAL VASCULAR, INC., Franklin Lakes, NJ (US)

(72) Inventors: Jordan Addison, Gilbert, AZ (US); Summer Ford, Queen Creek, AZ (US); Alexander Palmer, Scottsdale, AZ (US); Ryan Striedel, Tempe, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 155 days.

(21) Appl. No.: 17/772,903

(22) PCT Filed: Apr. 30, 2021

(86) PCT No.: PCT/US2021/030078
§ 371 (c)(1),
(2) Date: Apr. 28, 2022

(87) PCT Pub. No.: WO2022/231609
PCT Pub. Date: Nov. 3, 2022

(65) Prior Publication Data
US 2024/0156445 A1    May 16, 2024

(51) Int. Cl.
*A61B 10/02*    (2006.01)
*A61B 17/00*    (2006.01)
*A61B 17/34*    (2006.01)

(52) U.S. Cl.
CPC ........ *A61B 10/025* (2013.01); *A61B 17/3472* (2013.01); *A61B 2017/00367* (2013.01); *A61B 2017/00477* (2013.01)

(58) Field of Classification Search
CPC .............. A61B 10/025; A61B 17/3472; A61B 2017/00367; A61B 2017/00477
See application file for complete search history.

(56) References Cited

U.S. PATENT DOCUMENTS 7,850,620 B2    12/2010  Miller et al.
8,668,698 B2    3/2014   Miller et al.
(Continued)

FOREIGN PATENT DOCUMENTS

JP    2016513565 A    5/2016
WO    2014144797 A1   9/2014

OTHER PUBLICATIONS

International Search Report & Written Opinion dated Jan. 26, 2022, pertaining to PCT/US2021/030078.
(Continued)

*Primary Examiner* — Kevin T Truong
*Assistant Examiner* — Diana Jones
(74) *Attorney, Agent, or Firm* — Dinsmore & Shohl LLP

(57) ABSTRACT

A coupler device for interfacing between a biopsy driver and an intraosseous device includes a drive body having a distal drive receptacle. The drive body is rotatable around a longitudinal axis. The distal drive receptacle is configured to drivably couple to a drive portion of the intraosseous device. A distal coupler portion is coupled to the drive body and is configured to operate a distal latch member. The distal latch member latches the drive body to the intraosseous device when the distal coupler portion is in a distal coupler latch position. The distal coupler portion has a distal housing portion that is movable in either of a distal direction or a proximal direction. The distal coupler portion has a distal release position and a proximal release position. The distal housing portion is configured to move the distal coupler portion to a release position to operate the distal latch member.

21 Claims, 14 Drawing Sheets

(56) References Cited

U.S. PATENT DOCUMENTS

2009/0194446 A1* 8/2009 Miller .................... A61B 50/33
606/86 R
2011/0006489 A1 1/2011 Lai

OTHER PUBLICATIONS

Office Action date Dec. 12, 2024 pertaining to JP Application 2023-566570 filed Oct. 27, 2023.

* cited by examiner

BIOPSY SYSTEM AND COUPLER DEVICE FOR USE THEREWITH

CROSS-REFERENCE TO RELATED APPLICATIONS

This application is a U.S. national phase of International Application No. PCT/US2021/030078, filed Apr. 30, 2021, which is incorporated herein by reference in its entirety.

TECHNICAL FIELD

The present invention relates to a biopsy system, and, more particularly, to a biopsy system having a coupler device for interfacing between a driveshaft of a biopsy driver and a drive portion of an intraosseous device.

BACKGROUND ART

A bone biopsy surgical procedure involves the use of surgical devices for providing access to bone tissue, e.g., the cortical bone or bone marrow, of a patient. Such surgical devices may include a handheld motorized drill that may utilize an electric or pneumatic motor to rotate a cutting element of an intraosseous device, such as a biopsy needle. In some applications, means may be provided to releasably connect the biopsy needle to a driveshaft of the motorized drill. One such means is operable in a single direction to release the biopsy needle from the motorized drill to facilitate a substitution of the biopsy needle during the bone biopsy procedure.

What is needed in the art is a biopsy system having a coupler device for interfacing between a driveshaft of a biopsy driver and a drive portion of an intraosseous device, wherein the coupler device may be configured to facilitate a bidirectional (push-pull) release of the intraosseous device from the biopsy driver.

SUMMARY OF INVENTION

The present invention provides a biopsy system, and a coupler device for interfacing between a driveshaft of a biopsy driver and a drive portion of an intraosseous device, wherein the coupler device may be configured to facilitate a bidirectional (push-pull) release of the intraosseous device from the biopsy driver, in accordance with an aspect of the present invention.

The invention, according to one embodiment, is directed to a coupler device for interfacing between a driveshaft of a biopsy driver and a drive portion of an intraosseous device. The coupler device includes a drive body, a distal latch member, and a distal coupler portion. The drive body has a longitudinal axis and a distal drive receptacle. The drive body is rotatable around the longitudinal axis. The distal drive receptacle is configured to drivably couple to the drive portion of the intraosseous device. The distal latch member is coupled to the drive body. The distal coupler portion is coupled to the drive body and configured to operate the distal latch member. The distal coupler portion is associated with the distal drive receptacle. The distal latch member is configured to latch the drive body to the intraosseous device when the distal coupler portion is in a distal coupler latch position. The distal coupler portion has a distal housing portion that is movable in either of a distal direction or a proximal direction. The distal coupler portion is configured to have a distal release position and a proximal release position. The distal housing portion is configured to move in the distal direction to move the distal coupler portion to the distal release position to operate the distal latch member.

Similarly, the distal housing portion is configured to move in the proximal direction to move the distal coupler portion to the proximal release position to operate the distal latch member.

The invention, according to another embodiment, is directed to a biopsy system. The biopsy system includes a biopsy driver, an intraosseous device, and the coupler device of the invention referred to herein for coupling the biopsy driver to the intraosseous device.

An advantage of the present invention is that the coupler device may facilitate a bidirectional (push-pull) release of the intraosseous device from the biopsy driver.

Another advantage is that the distal housing portion may be pivoted around a longitudinal axis such that an external operator arm connected to the distal housing portion may be positioned to accommodate right-handed or left-handed operation of the distal coupler portion.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
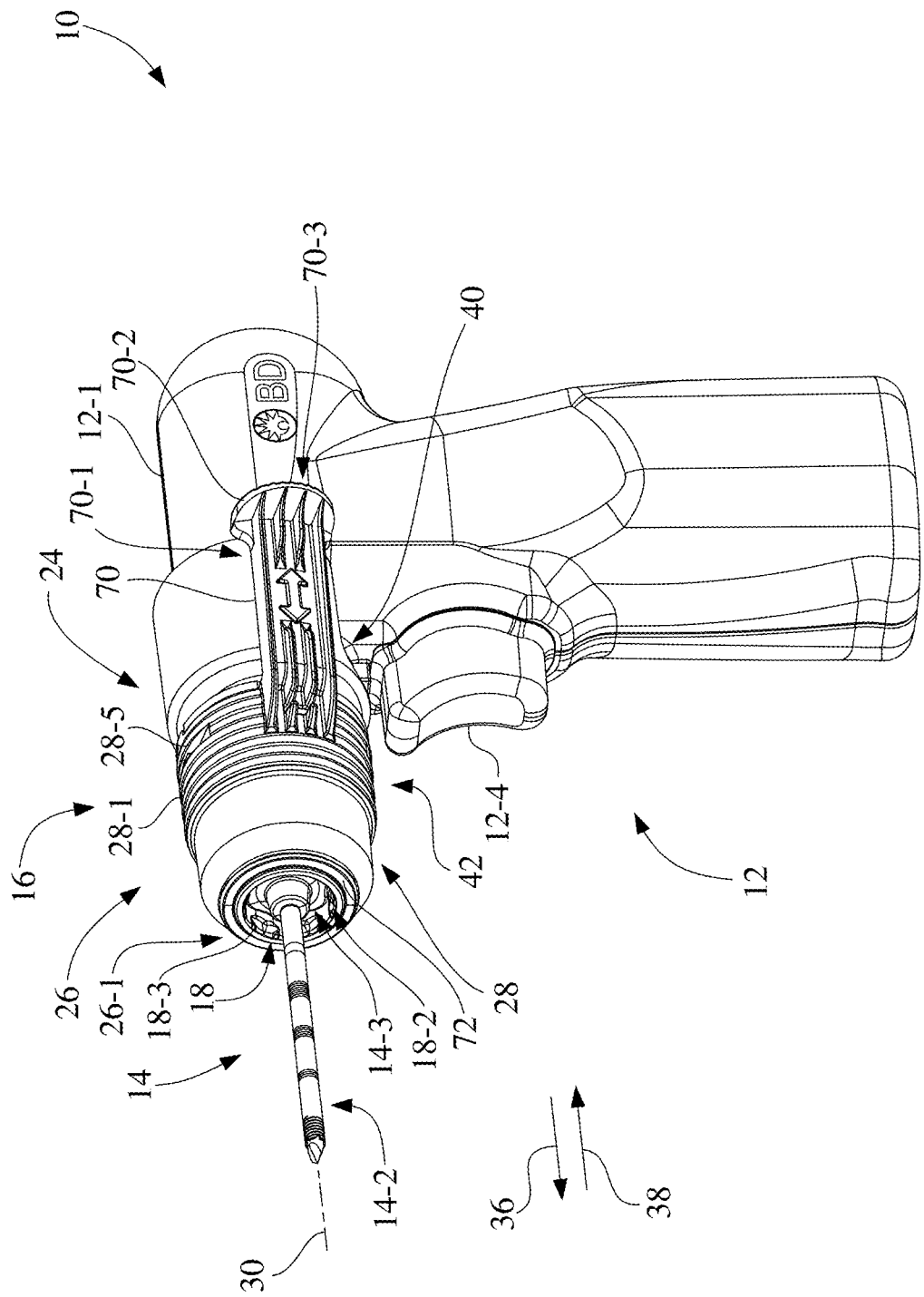
FIG. 1 is a perspective view of a biopsy system having a biopsy driver, an intraosseous device, and a coupler device having a proximal coupler portion and a distal coupler portion, with both coupler portions shown in a respective latched position.
Figure 2:
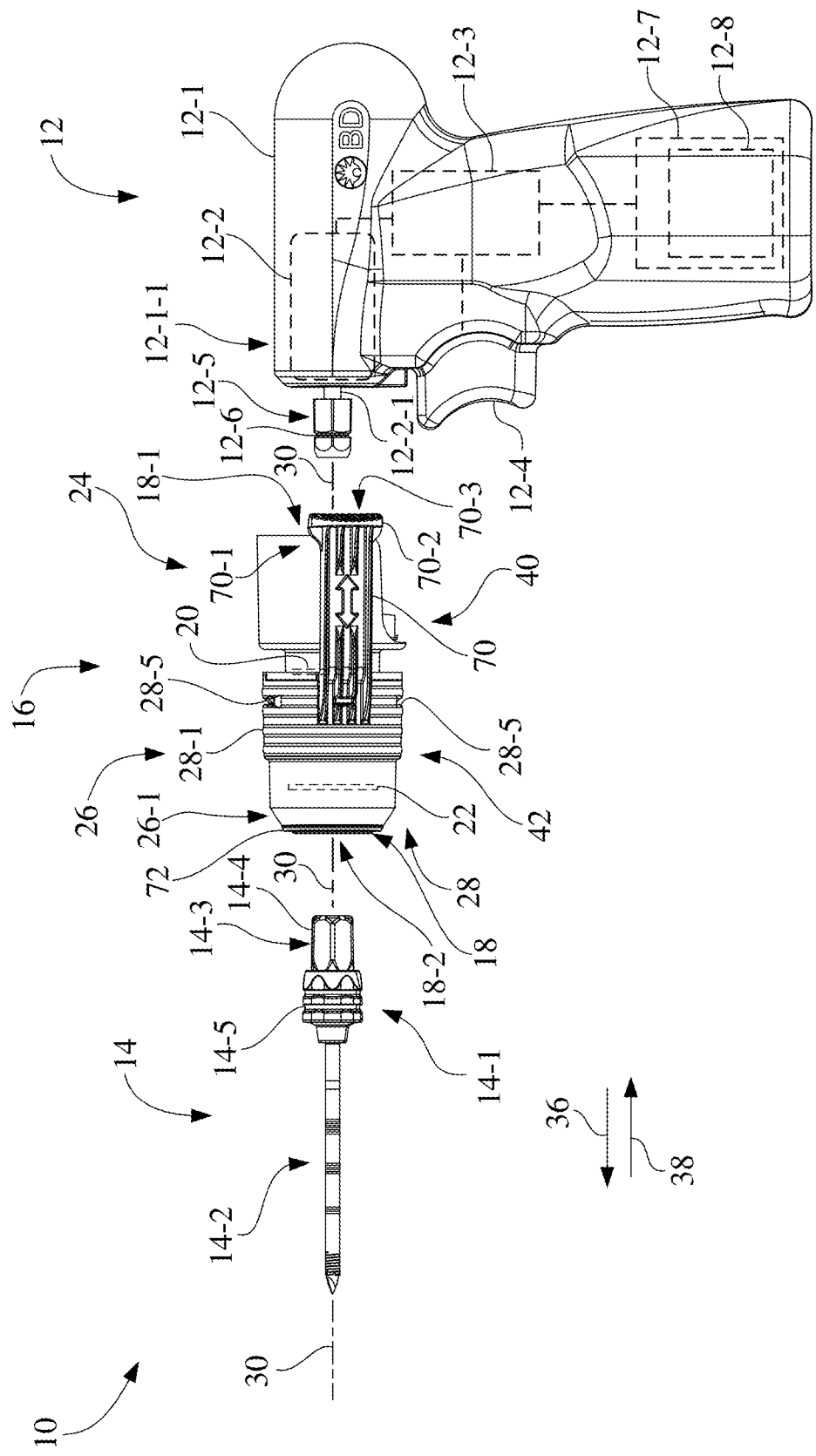
FIG. 2 is a side view of the biopsy system of FIG. 1, with the coupler device decoupled from each of the biopsy driver and the intraosseous device.

Referring to the drawings, and more particularly to FIGS. 1 and 2, there is shown a biopsy system 10 in accordance with an embodiment of the present invention. Biopsy system 10 includes a biopsy driver 12, an intraosseous device 14, and a coupler device 16. Biopsy driver 12 has a driveshaft 12-2-1. Intraosseous device 14 has a drive portion 14-1. Coupler device 16 is configured for interfacing between driveshaft 12-2-1 of biopsy driver 12 and drive portion 14-1 of intraosseous device 14, such that intraosseous device 14 may be coupled to biopsy driver 12 via coupler device 16 so as to facilitate intraosseous device 14 being rotationally driven by driveshaft 12-2-1 of biopsy driver 12.

Referring particularly to FIG. 2, biopsy driver 12 is configured to be handheld, i.e., grasped by the hand of a user, and may include a driver housing 12-1, a motor 12-2, a motor controller circuit 12-3, and a trigger 12-4, which are coupled to a driver housing 12-1. Motor 12-2 and motor controller circuit 12-3 are mounted within driver housing 12-1. Trigger 12-4 is movably coupled, e.g., in a slide mount or a pivot mount, to driver housing 12-1. Motor 12-2 may be, for example, a direct current (DC) motor, and driveshaft 12-2-1 of motor 12-2 may be configured to have a polygonal arrangement of drive surfaces 12-5, wherein the polygonal arrangement may be, for example, hexagonal. Driveshaft 12-2-1 includes an annular groove 12-6 that intersects a region of the polygonal arrangement of drive surfaces 12-5.

An on-board battery power supply 12-7 is connected in electrical communication with motor 12-2, motor controller circuit 12-3, and trigger 12-4. Electrical power may be supplied to motor 12-2, motor controller circuit 12-3, and trigger 12-4 via on-board battery power supply 12-7. In the present embodiment, on-board battery power supply 12-7 includes a battery 12-8, such as a permanent battery, or alternatively, a replaceable and/or rechargeable battery. Alternatively, an off-board power source, such as an alternating current (AC) wall outlet, may supply electrical power to biopsy driver 12.

Trigger 12-4 may be, for example, a slide rheostat, for supplying user input commands to motor controller circuit 12-3. Motor controller circuit 12-3 includes processing circuitry and power circuitry, so as to receive and process the user input commands from trigger 12-4, execute pre-installed program instructions, and supply power and operational signals to motor 12-2. The program instructions may include processor instructions to process the user input commands received from trigger 12-4 so as to select a desired rotational speed, and optionally may also select motor acceleration and/or torque profiles, for motor 12-2 having driveshaft 12-2-1. Driveshaft 12-2-1 includes an annular groove 12-6.

In the present embodiment, intraosseous device 14 is in the form of a bone biopsy needle assembly having a biopsy needle portion 14-2 connected to drive portion 14-1 of intraosseous device 14. Drive portion 14-1 may be configured to have an arrangement (e.g., a generally polygonal arrangement) of wavy driven surfaces 14-3. In the present embodiment, the arrangement of wavy driven surfaces 14-3 consist of alternating curved peaks and curved valleys around a perimeter 14-4 of drive portion 14-1.

Figure 3:
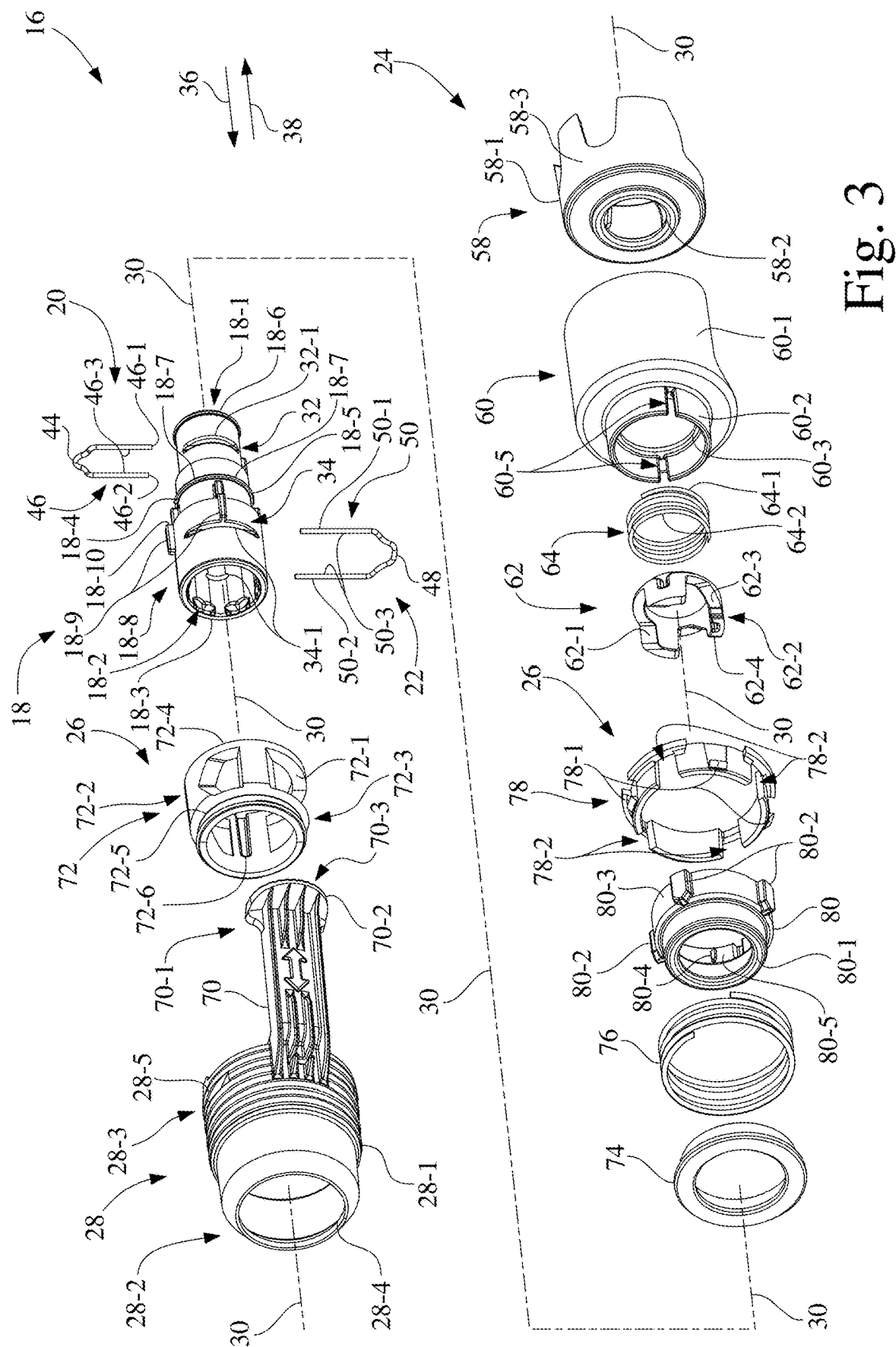
FIG. 3 is an exploded perspective view of the coupler device of FIGS. 1 and 2.

Referring to FIGS. 1-3, in the present embodiment, coupler device 16 includes a drive body 18, a proximal latch member 20, a distal latch member 22, a proximal coupler portion 24, and a distal coupler portion 26. Distal coupler portion 26 includes a distal housing portion 28. Each of proximal coupler portion 24 and distal coupler portion 26 is coupled to drive body 18. Proximal coupler portion 24 and distal coupler portion 26 and of coupler device 16 are configured to be operationally and structurally independent, although when used together, provide an additional functional aspect of accommodating a pivoting indexing of proximal coupler portion 24 relative to distal coupler portion 26.

Drive body 18 has a longitudinal axis 30, wherein drive body 18 is rotatable around longitudinal axis 30. Drive body 18 has a proximal drive receptacle 18-1, a distal drive receptacle 18-2, a distal end 18-3, an intermediate annular recess 18-4, an intermediate lip 18-5, and a proximal lip 18-6. Intermediate annular recess 18-4 is defined in part by intermediate lip 18-5. Intermediate lip 18-5 of drive body 18 also defines a spring engagement surface 18-7. As such, intermediate lip 18-5 resides between intermediate annular recess 18-4 and spring engagement surface 18-7.

Figure 6:
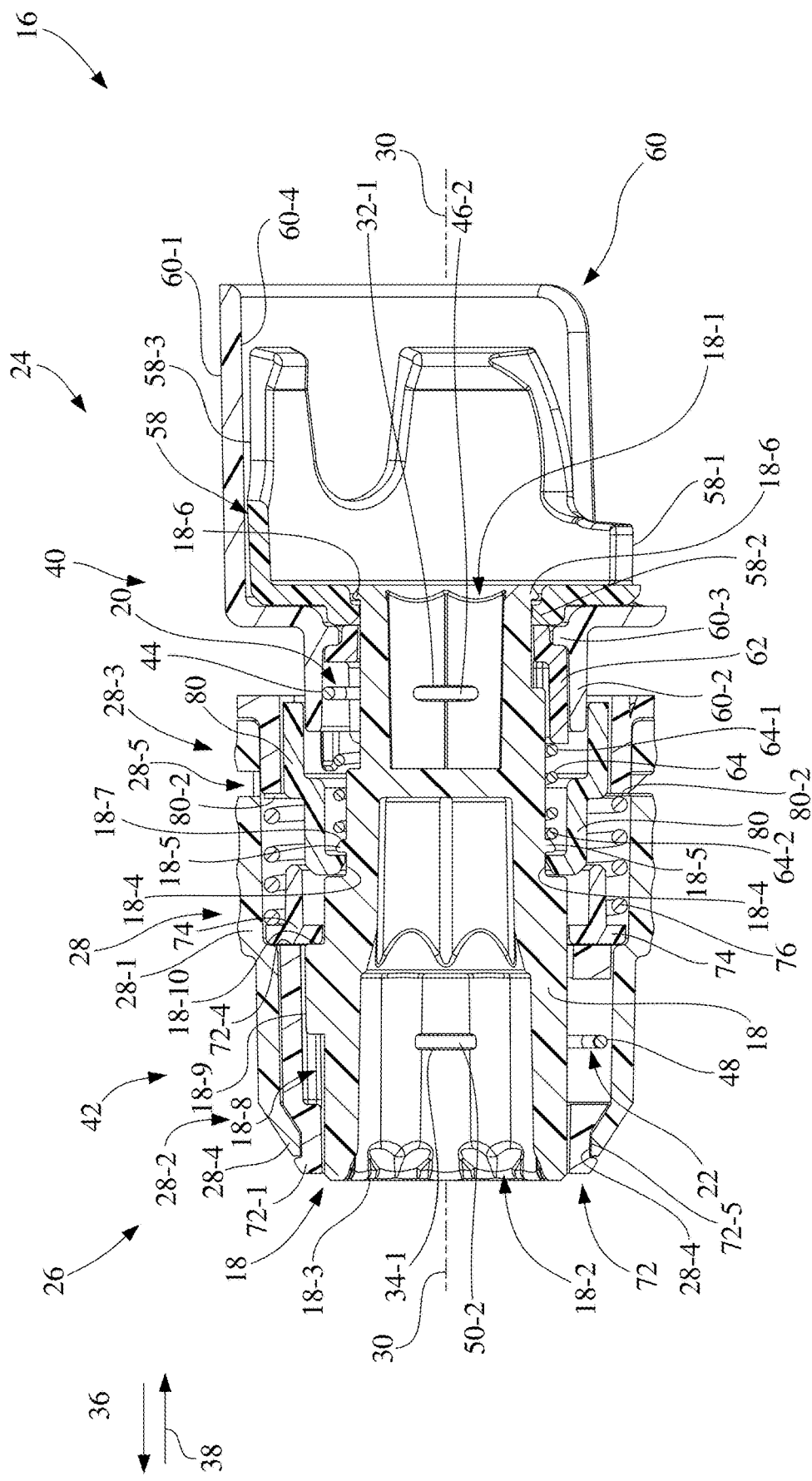
FIG. 6 is a section view of the coupler device taken along line 6-6 of FIG. 5, with the components of each of the proximal coupler portion and the distal coupler portion being in a respective latched position.
Figure 9:
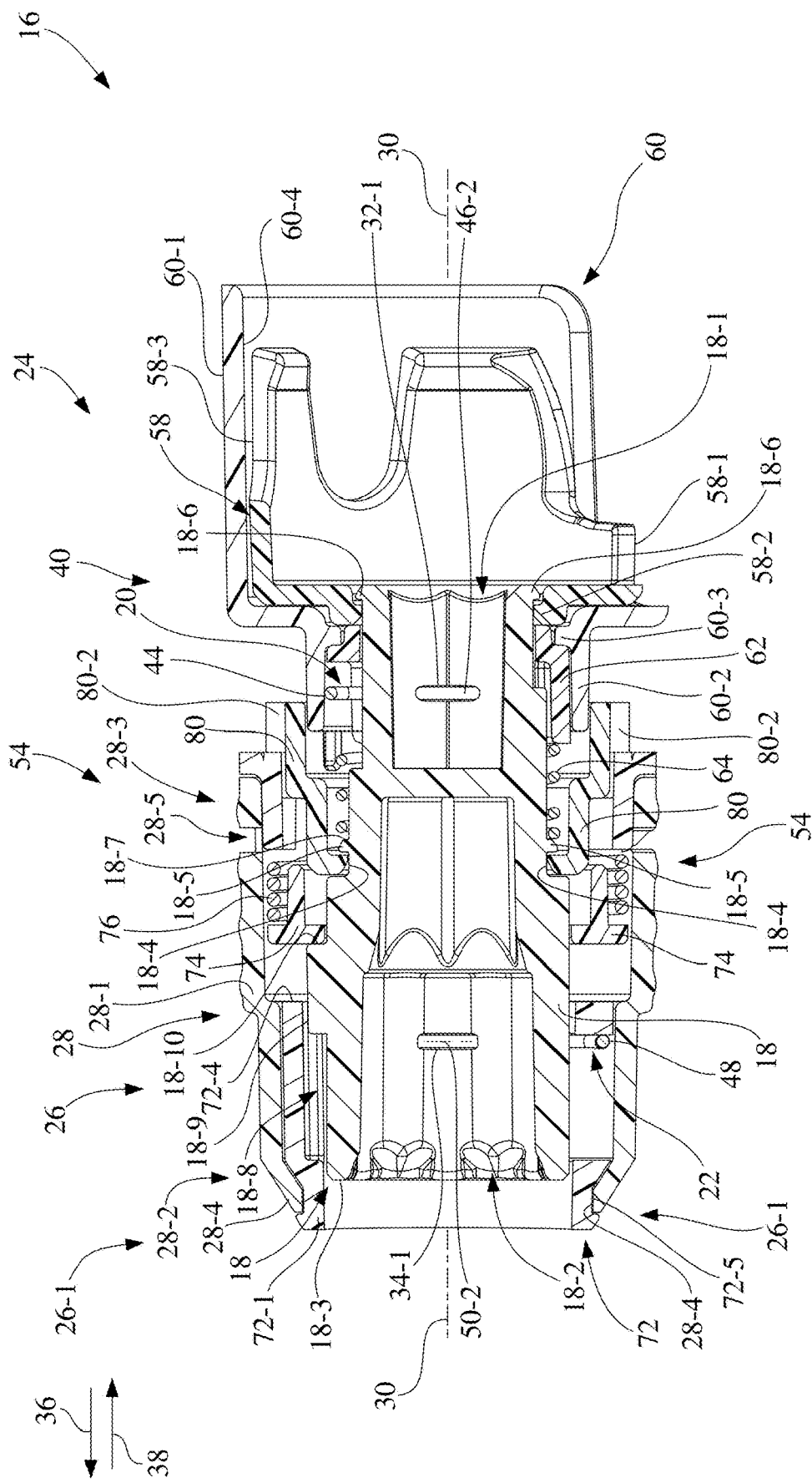
FIG. 9 is a section view of the coupler device taken along line 9-9 of FIG. 8, with the components of the proximal coupler portion being in the latched position, and the components of the distal coupler portion being in the distal release position.
Figure 12:
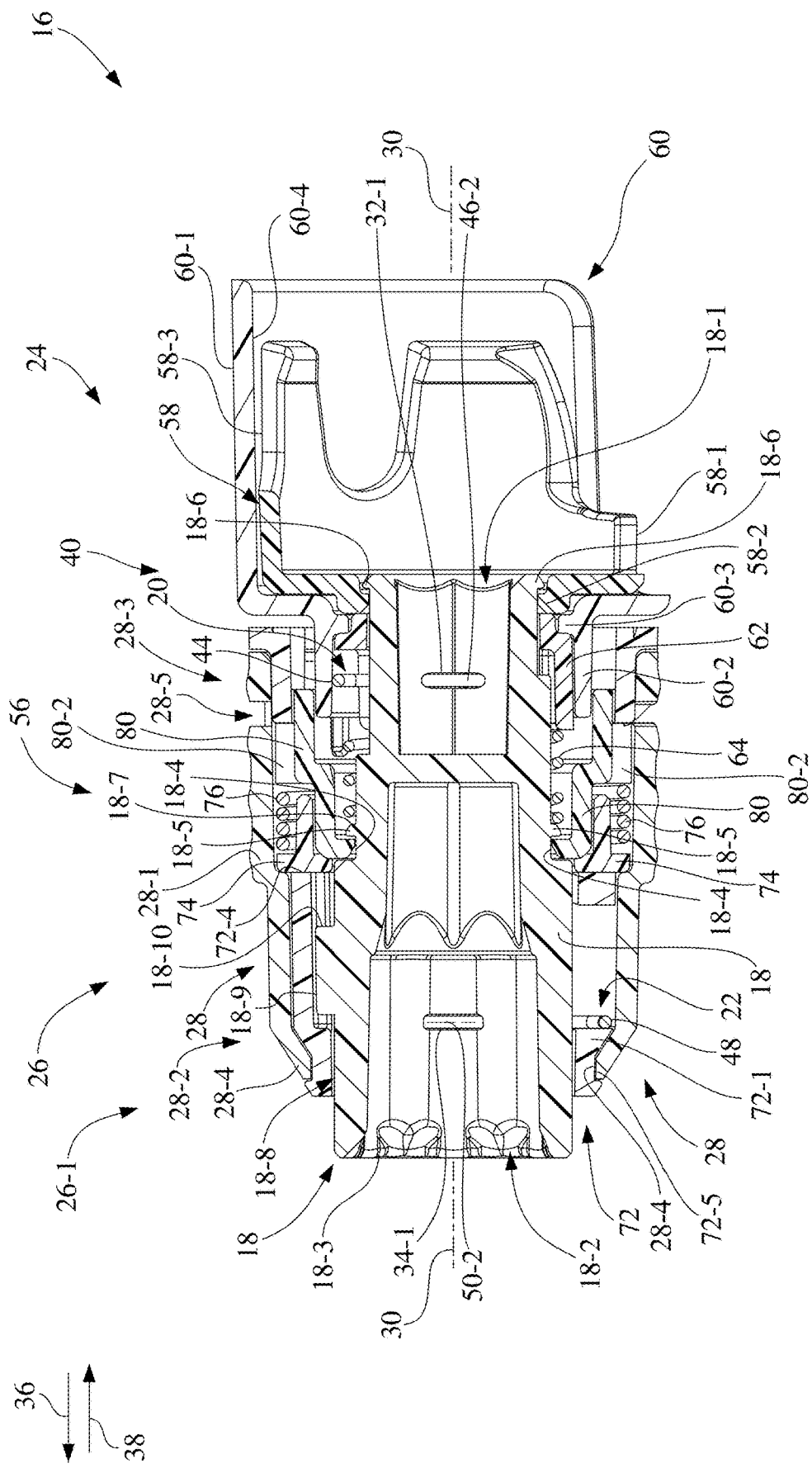
FIG. 12 is a section view of the coupler device taken along line 12-12 of FIG. 11, with the components of the proximal coupler portion being in the latched position and the components of the distal coupler portion being in the proximal release position.

Referring also to FIGS. 6, 9 and 12, distal drive receptacle 18-2 lies on longitudinal axis 30 in a distal cylindrical portion 18-8 of drive body 18. An exterior of distal cylindrical portion 18-8 of drive body 18 includes a plurality of longitudinally extending guide protrusion members 18-9. The exterior of distal cylindrical portion 18-8 of drive body 18 also includes a proximally facing surface 18-10, which for example, may be located (formed) at a proximal end of the plurality of longitudinally extending guide protrusion members 18-9.

Proximal drive receptacle 18-1 is associated with proximal coupler portion 24 and distal drive receptacle 18-2 is associated with distal coupler portion 26. Proximal drive receptacle 18-1 is configured, e.g., in size and in shape, to be coupled in driving engagement with, e.g., slidably receive, the polygonal arrangement of drive of surfaces 12-5 of driveshaft 12-2-1 of biopsy driver 12. Distal drive receptacle 18-2 is configured, e.g., in size and in shape, to drivably couple to, e.g., slidably receive, the arrangement of wavy driven surfaces 14-3 of drive portion 14-1 of intraosseous device 14.

Referring particularly to FIG. 3, drive body 18 further includes a proximal slotted region 32 and a distal slotted region 34. Distal slotted region 34 is longitudinally spaced from proximal slotted region 32 in a distal direction 36, and likewise, proximal slotted region 32 is longitudinally spaced from distal slotted region 34 in a proximal direction 38. Distal slotted region 34 is in distal cylindrical portion 18-8 of drive body 18.

Proximal slotted region 32 inwardly extends from an exterior surface of drive body 18 to proximal drive receptacle 18-1. Proximal slotted region 32 may be configured as a pair of diametrically opposed slots 32-1 (e.g., parallel vertical slots in the orientation as shown). Proximal slotted region 32 slidably receives proximal latch member 20 so as to axially restrain proximal latch member 20 relative to drive body 18 and to facilitate rotation of proximal latch member 20 in unison with drive body 18.

Likewise, distal slotted region 34 inwardly extends from an exterior surface of drive body 18 to distal drive receptacle 18-2. Distal slotted region 34 may be configured as a pair of diametrically opposed slots 34-1 (e.g., parallel vertical slots in the orientation as shown). Distal slotted region 34 slidably receives distal latch member 22 so as to axially restrain distal latch member 22 relative to drive body 18 and to facilitate rotation of distal latch member 22 in unison with drive body 18.

Each of FIGS. 1, 2, and 4-6 shows proximal coupler portion 24 and its corresponding components in a proximal coupler latch position 40, and also shows distal coupler portion 26 and its corresponding components in a distal coupler latch position 42. Proximal coupler portion 24 is coupled, e.g., slidably coupled, to drive body 18 and is configured to operate proximal latch member 20. Distal coupler portion 26 is coupled, e.g., slidably coupled, to drive body 18 and is configured to operate distal latch member 22.

Figure 4:
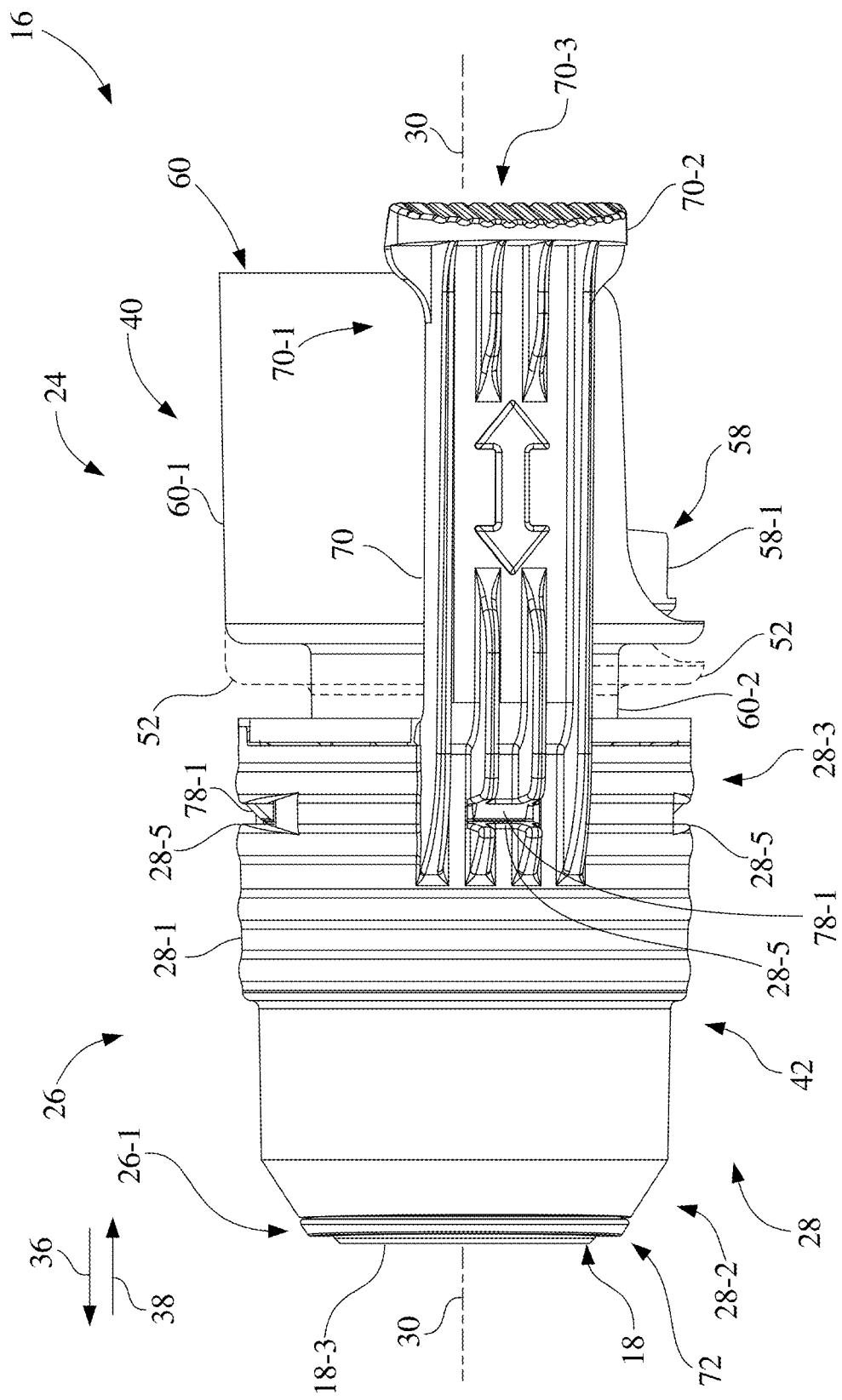
FIG. 4 is a side view of the coupler device of FIGS. 1-3, with each of the proximal coupler portion and the distal coupler portion being shown in a respective latched position, and further depicting by phantom lines a release position of the proximal coupler portion.
Figure 5:
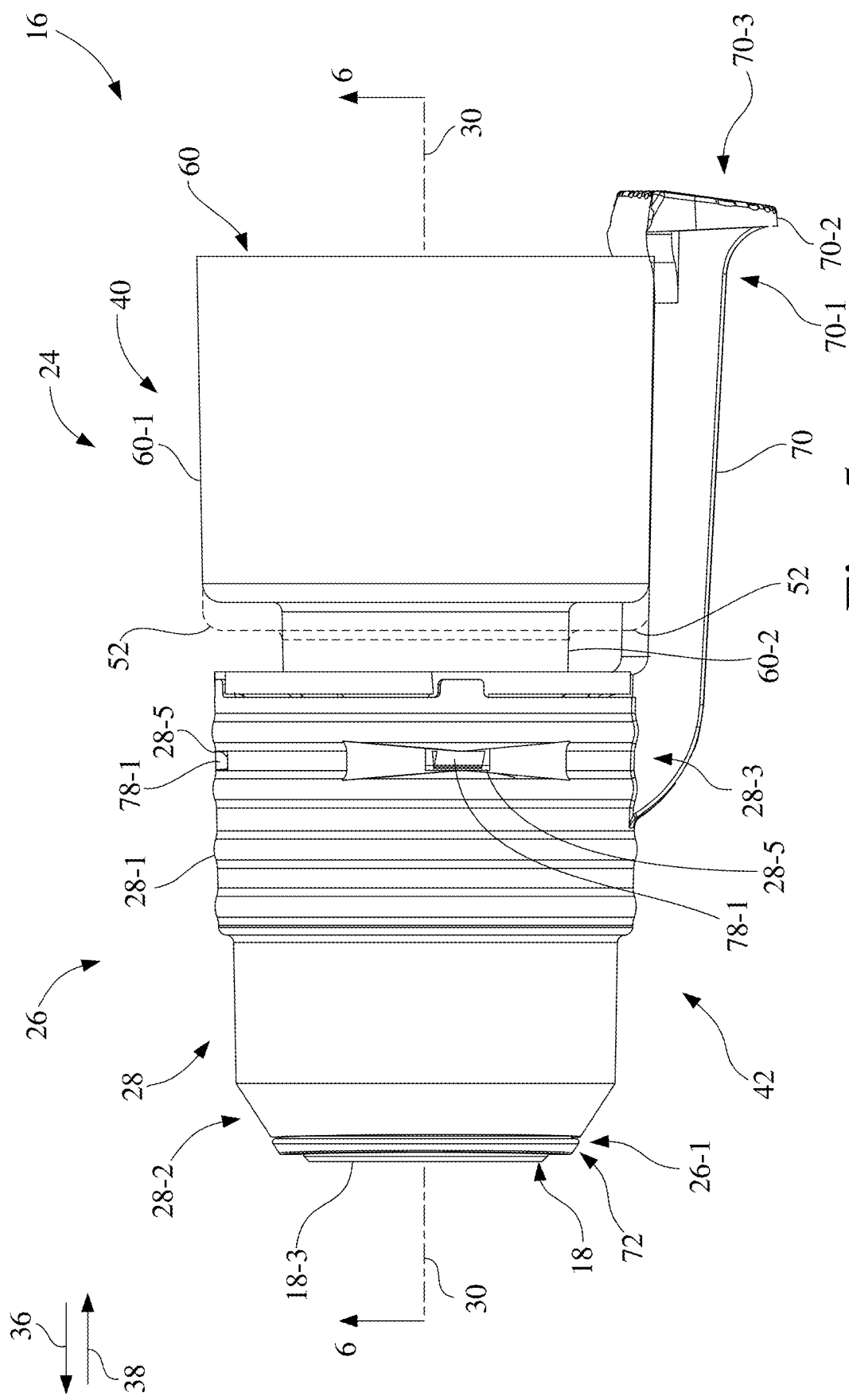
FIG. 5 is another side view of the coupler device of FIGS. 1-4, rotated 90 degrees around the longitudinal axis from the orientation shown in FIG. 4, with each of the proximal coupler portion and the distal coupler portion being shown in a respective latched position, and further depicting by phantom lines the release position of the proximal coupler portion.

Proximal latch member 20 is configured to latch drive body 18 to driveshaft 12-2-1 of biopsy driver 12 when proximal coupler portion 24 is in proximal coupler latch position 40, as depicted in FIGS. 1, 2, and 4-6. Referring particularly to FIG. 4-5, proximal latch member 20 is configured to release driveshaft 12-2-1 of biopsy driver 12 when proximal coupler portion 24 is in a first release position 52 (depicted by phantom lines), e.g., by moving proximal coupler portion 24 in distal direction 36 relative to drive body 18, so as to facilitate removal of coupler device 16 from biopsy driver 12.

Referring again to FIG. 3, proximal latch member 20 is a proximal U-shaped member having a head portion 44 and a pair of legs 46, individually identified as leg 46-1 and leg 46-2. For convenience, proximal U-shaped member will be referred to hereinafter as proximal U-shaped member 20. The pair of legs 46 of proximal U-shaped member 20 are configured, e.g., in size and in shape, to be received in the pair of diametrically opposed slots 32-1 of proximal slotted region 32 of drive body 18.

The pair of legs 46 of proximal U-shaped member 20 have an interior surface 46-3, wherein interior surface 46-3 is a surface on proximal U-shaped member 20 that is between leg 46-1 and leg 46-2. In the present embodiment, the pair of legs 46 of proximal U-shaped member 20 are parallel, i.e., leg 46-1 is parallel to leg 46-2, or at least substantially parallel.

Referring to FIGS. 2 and 3 in conjunction with FIG. 4, when proximal coupler portion 24 is in proximal coupler latch position 40, the pair of legs 46 of proximal U-shaped member 20 extend into proximal drive receptacle 18-1 of drive body 18 (see also FIG. 6; leg 46-2 shown), and thus is configured to engage annular groove 12-6 (see FIG. 2) in driveshaft 12-2-1 of biopsy driver 12 so as to latch coupler device 16 to driveshaft 12-2-1 of biopsy driver 12.

Referring again to FIGS. 1, 2, and 4-6, distal latch member 22 is configured to latch drive body 18 to intraosseous device 14 when distal coupler portion 26 is in distal coupler latch position 42. Referring again to FIG. 3, in the present embodiment, distal latch member 22 is a distal U-shaped member. For convenience, distal U-shaped member 22 will be referred to hereinafter as distal U-shaped member 22. Distal U-shaped member 22 has a head portion 48 and a pair of legs 50, individually identified as leg 50-1 and leg 50-2.

The pair of legs 50 of distal U-shaped member 22 have an interior surface 50-3, wherein interior surface 50-3 is the surface on distal U-shaped member 22 that is between leg 50-1 and leg 50-2. In the present embodiment, the pair of legs 50 of distal U-shaped member 22 are parallel, i.e., leg 50-1 is parallel to leg 50-2, or at least substantially parallel. The pair of legs 50 of distal U-shaped member 22 are configured, e.g., in size and in shape, to be received in the pair of diametrically opposed slots 34-1 of distal slotted region 34 of drive body 18.

Referring to FIGS. 2 and 3 in conjunction with FIG. 4, when distal coupler portion 26 is in distal coupler latch position 42, the pair of legs 50 of distal U-shaped member 22 extend into distal drive receptacle 18-2 of drive body 18 (see also FIG. 6; leg 50-2 shown). Thus, the pair of legs 50 of distal U-shaped member 22 is configured to engage an annular groove 14-5 (see FIG. 2) in drive portion 14-1 of intraosseous device 14 so as to latch coupler device 16 to drive portion 14-1 of intraosseous device 14 when distal coupler portion 26 is in distal coupler latch position 42.

Figure 7:
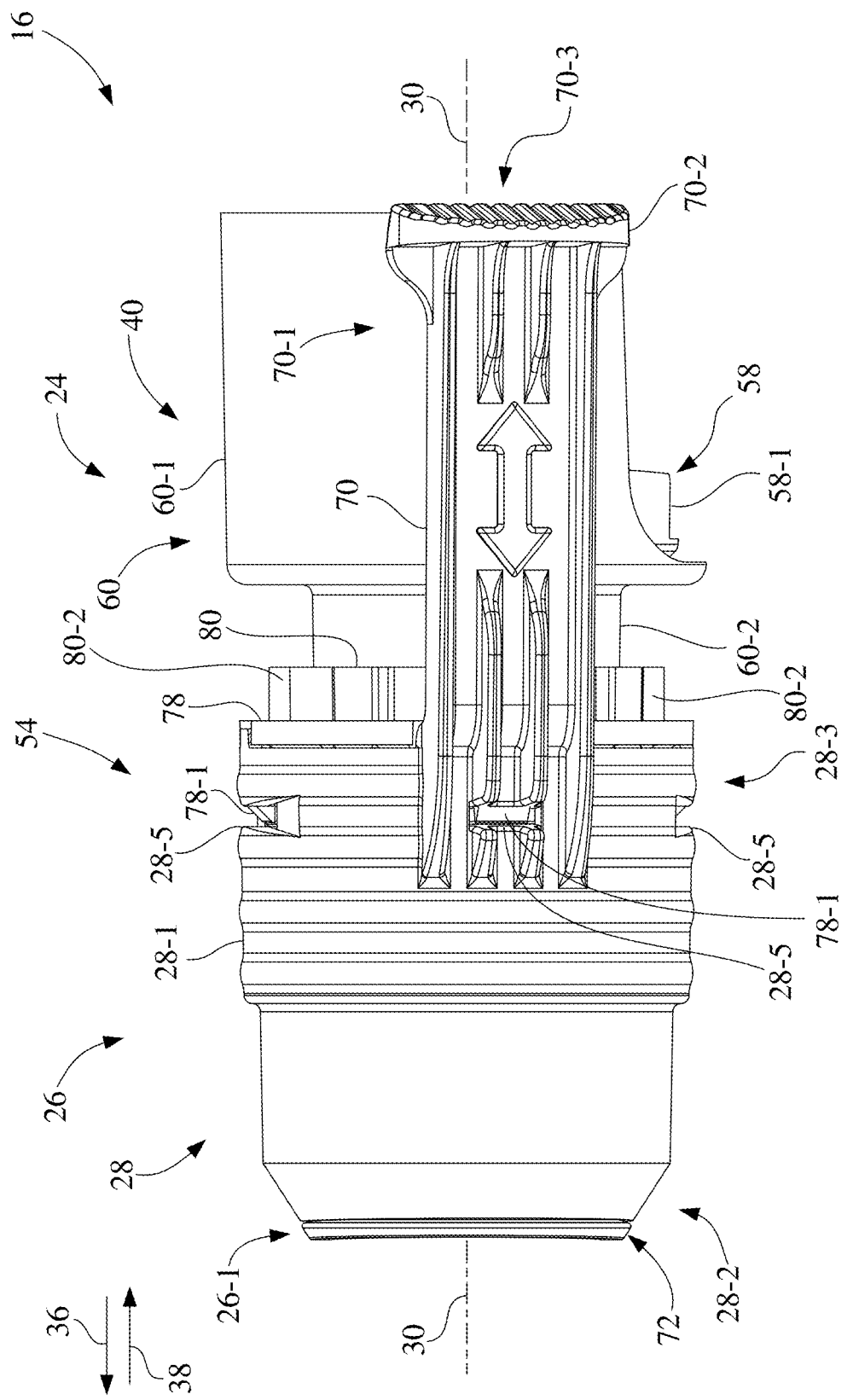
FIG. 7 is a side view of the coupler device of FIGS. 1-6, with the proximal coupler portion being in the latched position and the distal coupler portion being in a distal release position.
Figure 8:
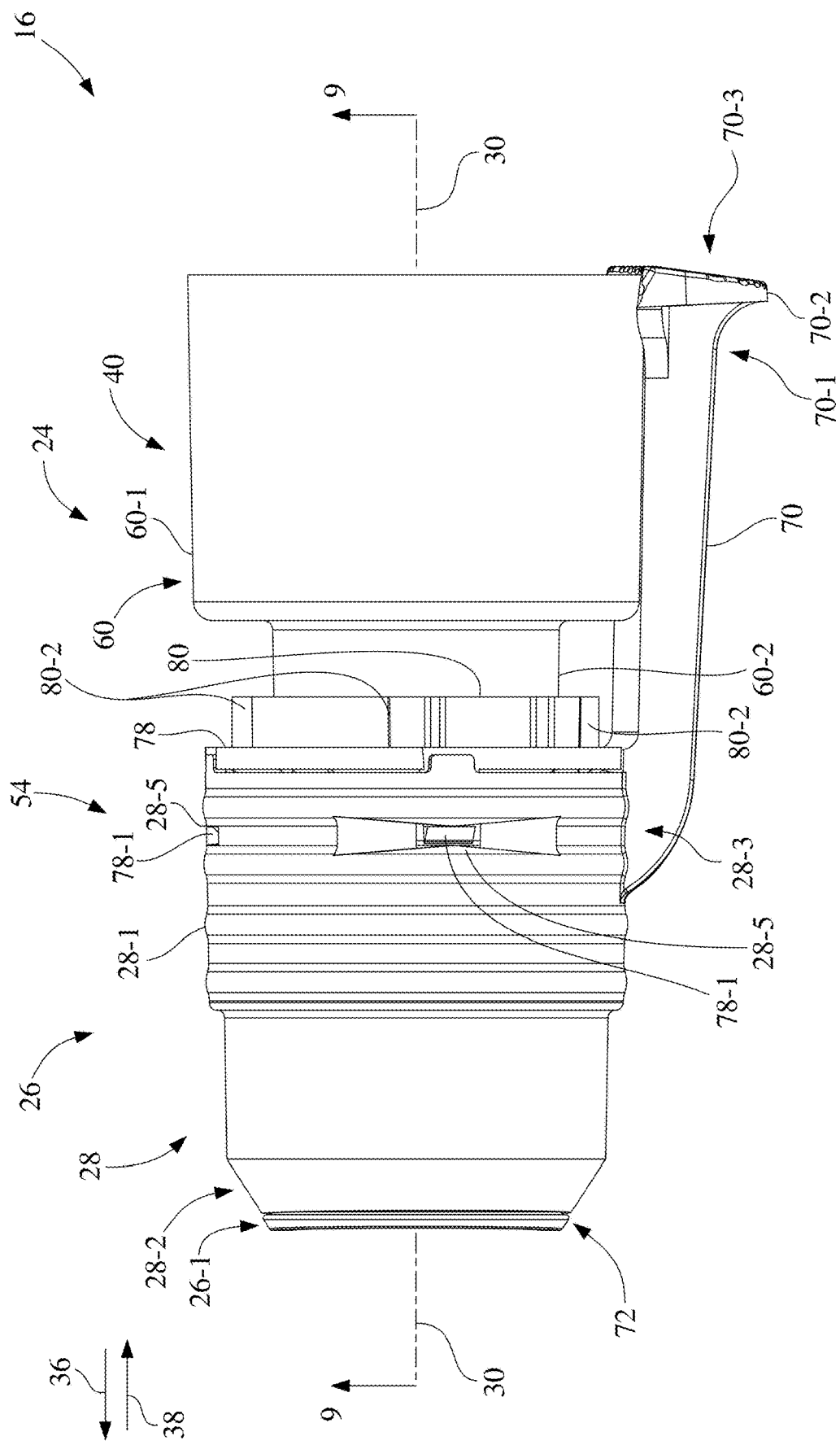
FIG. 8 is another side view of the coupler device rotated 90 degrees around the longitudinal axis from the orientation shown in FIG. 7, with the proximal coupler portion being in the latched position and the distal coupler portion being in the distal release position.
Figure 10:
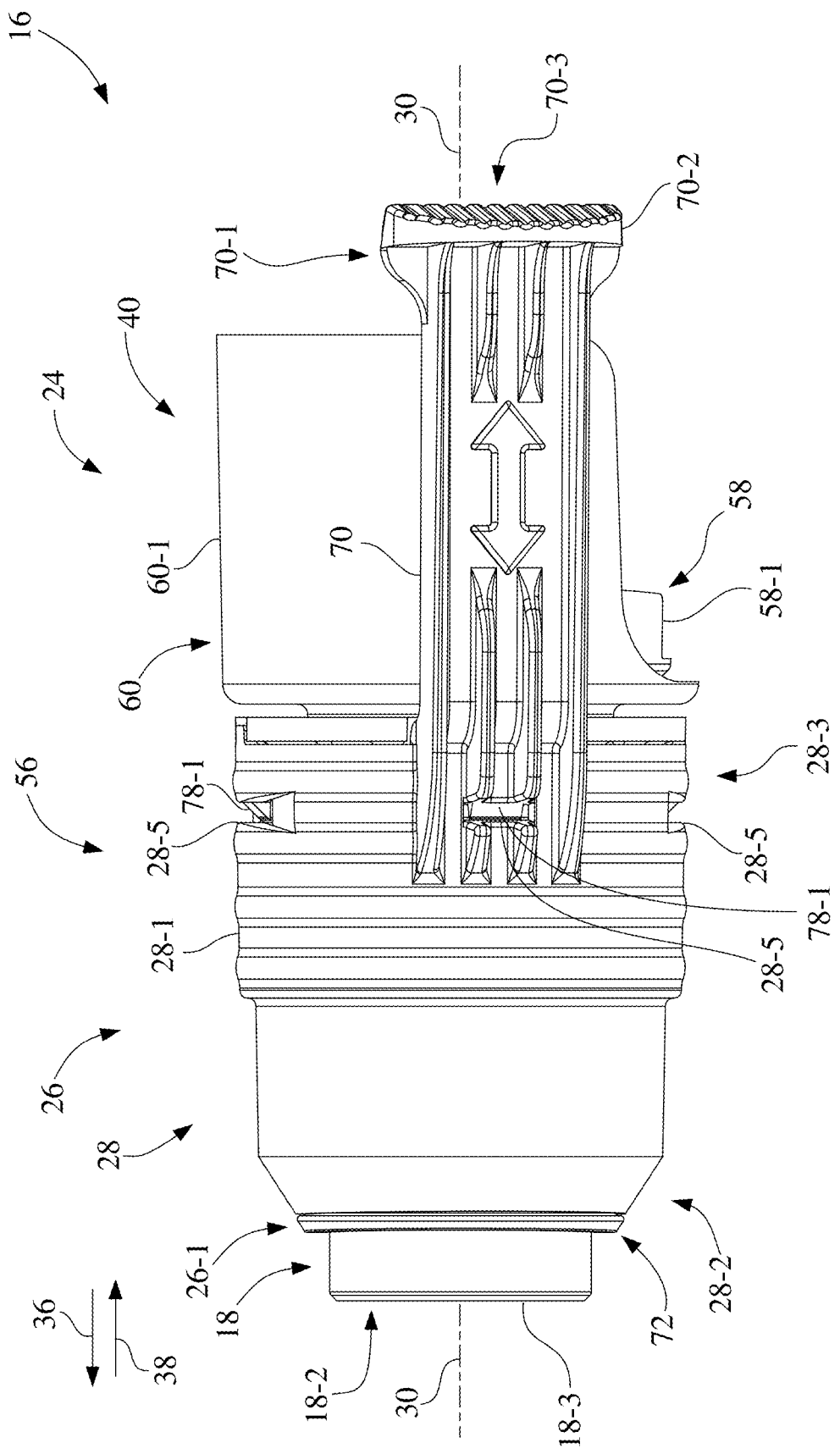
FIG. 10 is a side view of the coupler device of FIGS. 1-6, with the proximal coupler portion being in the latched position and the distal coupler portion being in a proximal release position.
Figure 11:
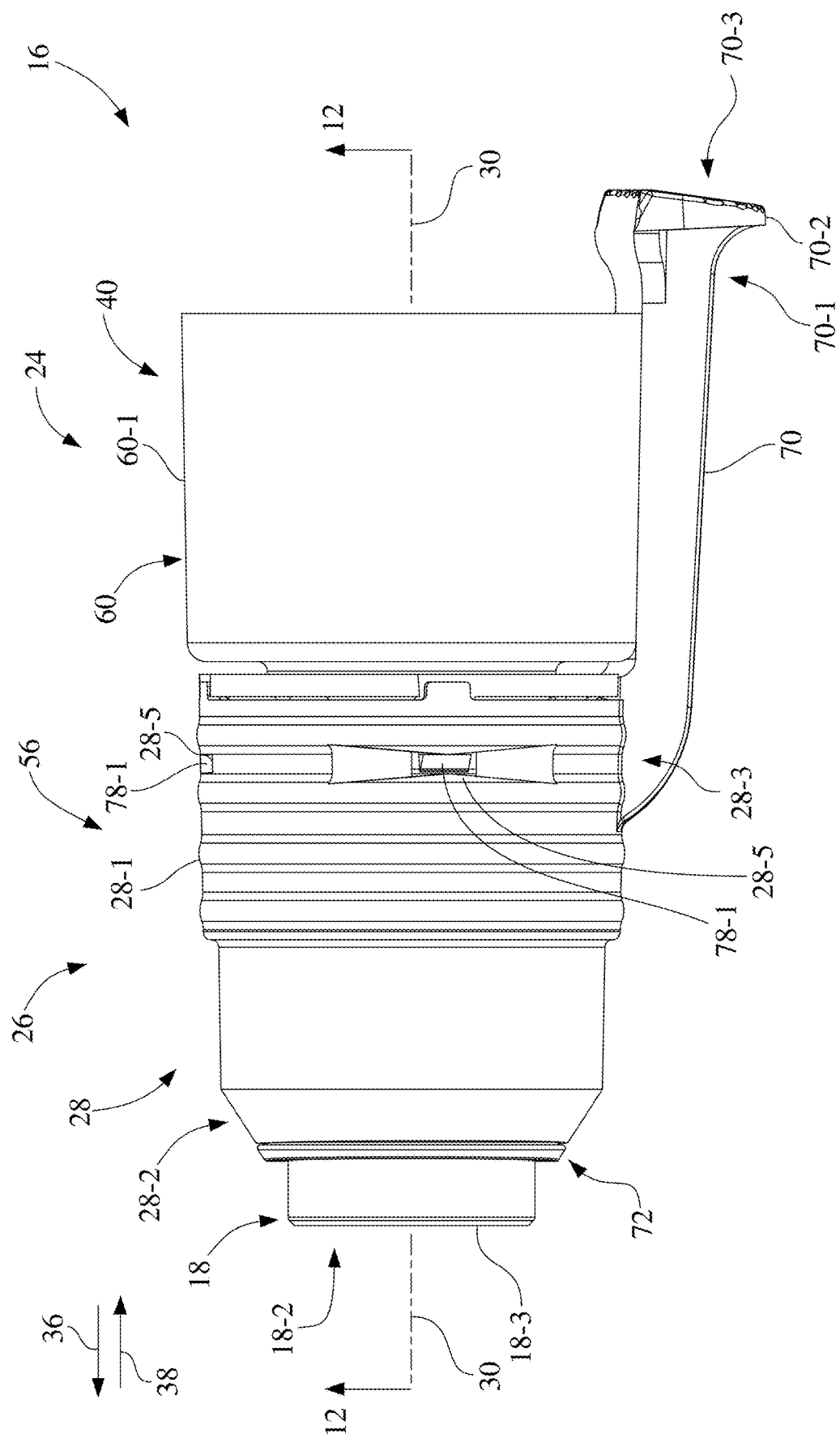
FIG. 11 is another side view of the coupler device rotated 90 degrees around the longitudinal axis from the orientation shown in FIG. 10, with the proximal coupler portion being in the latched position and the distal coupler portion being in the proximal release position.

Distal coupler portion 26, having distal housing portion 28, is movable in either of distal direction 36 or a proximal direction 38. In other words, distal coupler portion 26 is bidirectionally operable. Distal coupler portion 26 has a distal release position 54 (see FIGS. 7-9) and a proximal release position 56 (see FIGS. 10-12). With reference to distal coupler portion 26 being in distal coupler latch position 42, as depicted in FIGS. 1, 2, 4-6, distal housing portion 28 is movable in distal direction 36 to move distal coupler portion 26 to distal release position 54 (see FIGS. 7-9) so as to release distal latch member 22 (e.g., distal U-shaped member 22) from intraosseous device 14. Conversely, distal housing portion 28 is movable in proximal direction 38 to move distal coupler portion 26 to proximal release position 56 (see FIGS. 10-12) to release distal latch member 22 (e.g., distal U-shaped member 22) from intraosseous device 14. In other words, distal coupler portion 26 is bidirectionally operable, e.g., by a proximal or distal movement of distal housing portion 28, so as to release distal latch member 22 (e.g., distal U-shaped member 22) from intraosseous device 14 to facilitate removal of intraosseous device 14 from coupler device 16.

Referring FIG. 9, in the present embodiment, when distal coupler portion 26 is in distal release position 54, a distal end 26-1 of distal coupler portion 26 axially extends in distal direction 36 beyond distal end 18-3 of drive body 18. Moreover, referring to FIGS. 3 and 9, when distal coupler portion 26 is in distal release position 54, the pair of legs 50 (leg 50-2 shown in FIG. 9) of distal U-shaped member 22 are radially retracted from distal drive receptacle 18-2 of drive body 18, although the pair of legs 50 of distal U-shaped member 22 remain engaged with the pair of diametrically opposed slots 34-1 of drive body 18 (see FIG. 9; leg 50-2 shown through one of the pair of diametrically opposed slots 34-1). Thus, when distal coupler portion 26 is in distal release position 54, distal U-shaped member 22 (and more particularly the pair of legs 50) is configured to disengage annular groove 14-5 (see FIG. 2) in drive portion 14-1 of intraosseous device 14 so as to facilitate removal of intraosseous device 14 from distal coupler portion 26 of coupler device 16.

Referring to FIG. 12, in the present embodiment, when distal coupler portion 26 is in proximal release position 56, distal end 26-1 of distal coupler portion 26 is retracted in distal direction 36 relative to distal end 18-3 of drive body 18. Moreover, referring to FIGS. 3 and 12, when distal coupler portion 26 is in proximal release position 56, the pair of legs 50 of distal U-shaped member 22 are radially retracted from distal drive receptacle 18-2 of drive body 18, although the pair of legs 50 of distal U-shaped member 22 remain engaged with the pair of diametrically opposed slots 34-1 of drive body 18 (see FIG. 12; leg 50-2 shown through one of the pair of diametrically opposed slots 34-1). Thus, when distal coupler portion 26 is in proximal release position 56, distal U-shaped member 22 (and more particularly the pair of legs 50) is configured to disengage annular groove 14-5 (see FIG. 2) in drive portion 14-1 of intraosseous device 14 so as to facilitate removal of intraosseous device 14 from distal coupler portion 26 of coupler device 16.

Referring again to FIGS. 3-6, proximal coupler portion 24 includes a proximal retainer member 58, a proximal housing portion 60, a proximal release sleeve 62, and a proximal portion spring 64. Proximal housing portion 60, proximal release sleeve 62, and proximal portion spring 64 are axially interposed between proximal retainer member 58 and intermediate lip 18-5 of drive body 18.

Proximal retainer member 58 includes a neck portion 58-1 and an annular retention lip 58-2. Neck portion 58-1 has an outer periphery surface 58-3. Annular retention lip 58-2 extends radially inwardly toward longitudinal axis 30. Annular retention lip 58-2 is configured for axial connective engagement with proximal lip 18-6 of drive body 18, which cooperate to proximally retrain proximal coupler portion 24 on drive body 18 in proximal direction 38.

Proximal housing portion 60 includes a collar portion 60-1, a cylindrical extension 60-2, and an annular lip 60-3. Annular lip 60-3 is located at the junction of collar portion 60-1 and cylindrical extension 60-2. Proximal housing portion 60 is proximally engaged by proximal retainer member 58, e.g., by engagement of annular retention lip 58-2 of proximal retainer member 58 with annular lip 60-3 of proximal housing portion 60. Proximal housing portion 60 is configured, e.g., in size and in shape, to radially surround proximal release sleeve 62 and proximal latch member 20. More particularly, cylindrical extension 60-2 of proximal housing portion 60 is configured, e.g., in size and in shape, to radially surround proximal release sleeve 62 and proximal latch member 20.

Referring to FIG. 6, collar portion 60-1 has an inner periphery surface 60-4. In some embodiments, a driver containment bag (not shown; to contain biopsy driver 12) may be mounted to proximal coupler portion 24 by inserting a portion of the driver containment bag between inner periphery surface 60-4 of collar portion 60-1 of proximal housing portion 60 and outer periphery surface 58-3 of neck portion 58-1 of proximal retainer member 58.

Referring to FIG. 6, with reference to FIGS. 1 and 2, at least one of neck portion 58-1 of proximal retainer member 58 and/or collar portion 60-1 of proximal housing portion 60 may be configured, e.g., in size and in shape, to engage driver housing 12-1, e.g., in a surface-to-surface contact, to prevent proximal coupler portion 24 of coupler device 16 from rotating relative to driver housing 12-1 of biopsy driver 12. For example, inner periphery surface 60-4 of collar portion 60-1 of proximal housing portion 60 may be configured, e.g., in size and in shape, to engage a distal exterior portion 12-1-1 (see FIG. 2) of driver housing 12-1 of biopsy driver 12 in a surface-to-surface contact so as to prevent proximal coupler portion 24 of coupler device 16 from rotating relative to driver housing 12-1 of biopsy driver 12.

Referring again to FIG. 3, cylindrical extension 60-2 of proximal housing portion 60 includes a plurality of indexing openings 60-5 around a periphery of cylindrical extension 60-2. The plurality of indexing openings 60-5 of cylindrical extension 60-2 of proximal housing portion 60 may be utilized to rotationally index proximal coupler portion 24 to distal coupler portion 26 at multiple discrete angular intervals around longitudinal axis 30. In the present embodiment, the plurality of indexing openings 60-5 is represented in FIG. 3 as two diametrically opposed slots, e.g., at a 180 degree spacing. However, for some applications it may be desired that the two slots may be non-diametrically opposed. In addition, for some applications, the plurality of indexing openings 60-5 may include three or more slots, which may be spaced angularly equidistant, or alternatively non-equidistant, around a periphery of cylindrical extension 60-2 of proximal housing portion 60.

Referring to FIGS. 3 and 6, proximal release sleeve 62 is configured, e.g., in size and in shape, to be axially slidable along drive body 18. With further reference to FIGS. 4 and 5, in the present embodiment, proximal housing portion 60 is configured to engage proximal release sleeve 62 to axially slide proximal release sleeve 62 of proximal coupler portion 24 from proximal coupler latch position 40 to first release position 52 so as to operate proximal latch member 20 to release drive body 18 from driveshaft 12-2-1 of biopsy driver 12 to facilitate removal of coupler device 16 from biopsy driver 12. Stated differently, as a user applies a distally directed force to proximal housing portion 60, proximal housing portion 60 moves in distal direction 36 and in turn, proximal release sleeve 62 is moved by proximal housing portion 60 in distal direction 36 so as to operate proximal latch member 20.

Figure 13:
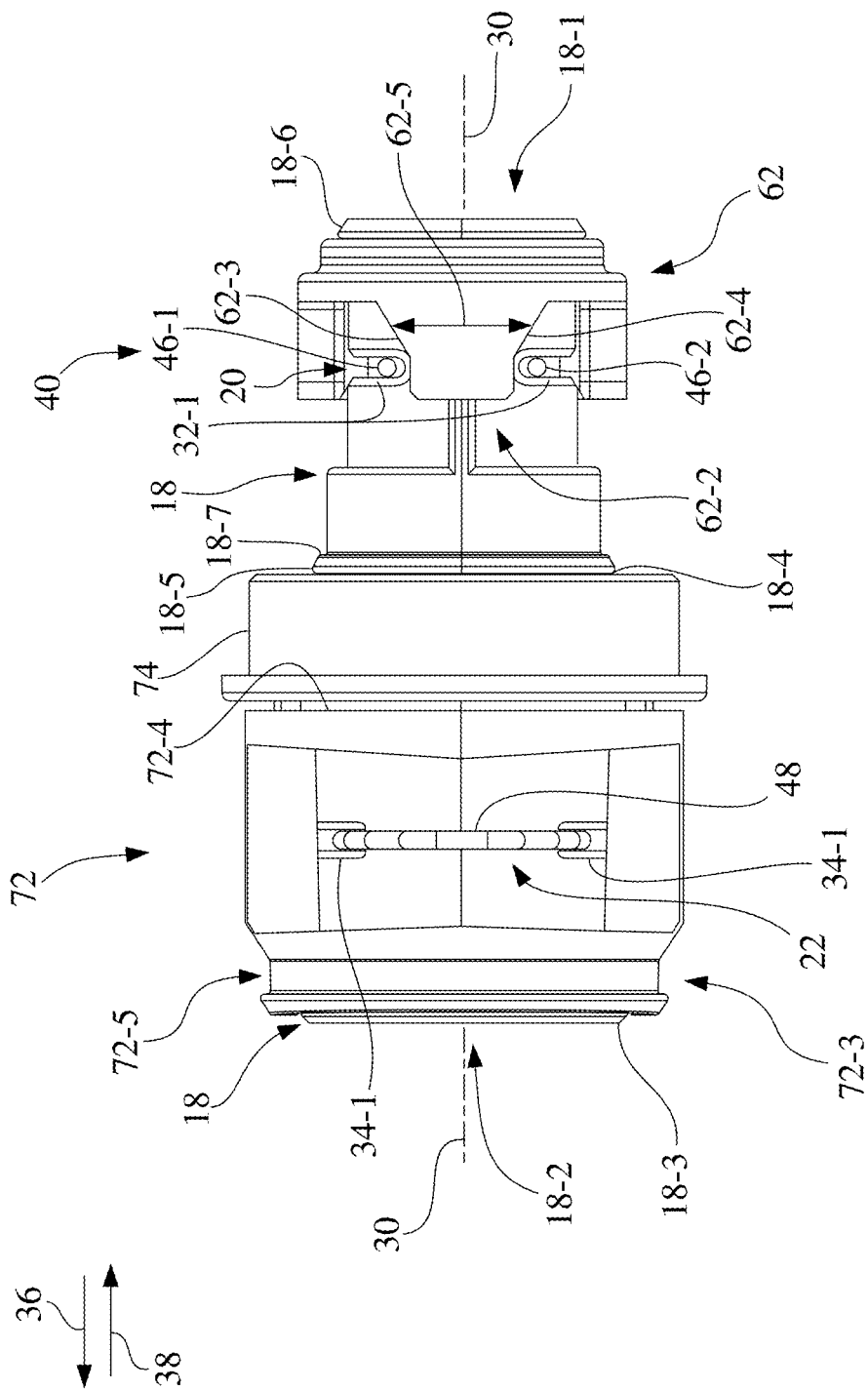
FIG. 13 is a side view of a portion of the coupler device of FIGS. 1-6, with the proximal and distal housing portions removed, and oriented to show a proximal wedge member of a proximal release sleeve of the proximal coupler portion positioned on a drive body of the coupler device, and with the proximal release sleeve and a proximal latch member in the latched position.

Referring to FIG. 3, proximal release sleeve 62 has a generally cylindrical shape having a side wall 62-1 with portions removed to define a proximal wedge member 62-2 at side wall 62-1. Referring also to FIG. 13, proximal wedge member 62-2 includes a first tapered surface 62-3 and a second tapered surface 62-4, wherein collectively, first tapered surface 62-3 and second tapered surface 62-4 tend to converge in distal direction 36 and, conversely, tend to diverge in proximal direction 38, in the orientation shown. Proximal wedge member 62-2 is configured, e.g., in size and in shape, to apply an outwardly directed force to interior surface 46-3 (see FIG. 3) of the pair of legs 46 of proximal U-shaped member 20 to spread the pair of legs 46 of proximal U-shaped member 20 apart to cause the pair of legs 46 of proximal U-shaped member 20 to disengage from annular groove 12-6 (see FIG. 2) in driveshaft 12-2-1 of biopsy driver 12 when proximal release sleeve 62 of proximal coupler portion 24 is axially moved in distal direction 36 from proximal coupler latch position 40 to first release position 52 (see also FIGS. 4 and 5).

Accordingly, with reference to FIG. 13, as proximal release sleeve 62 of proximal coupler portion 24 is axially moved in distal direction 36, a distance 62-5 between first tapered surface 62-3 and a second tapered surface 62-4 increases at the points of intersection of proximal wedge member 62-2 with the pair of legs 46 of proximal latch member 20 so as to, in turn, increase the spacing between leg 46-1 and leg 46-2 of the pair of legs 46 of proximal latch member 20. This increase of spacing between leg 46-1 and leg 46-2 then outwardly moves the pair of legs 46 in the pair of diametrically opposed slots 32-1 of proximal slotted region 32 (see FIG. 3 with reference to FIG. 6) of drive body 18, which in turn radially withdraws the pair of legs 46 of proximal latch member 20 from proximal drive receptacle 18-1 so as to facilitate removal of coupler device 16 from driveshaft 12-2-1 of biopsy driver 12 (see FIG. 2).

Referring to FIGS. 3 and 6 (with reference to FIGS. 4 and 5), proximal portion spring 64 is configured, e.g., in size and in shape, to axially bias proximal release sleeve 62 of proximal coupler portion 24 in proximal direction 38 to proximal coupler latch position 40. Proximal portion spring 64 may be, for example, a coil spring having a proximal end 64-1 and a distal end 64-2. In the present embodiment, proximal portion spring 64 is interposed between proximal release sleeve 62 of proximal coupler portion 24 and intermediate lip 18-5 of driver body 18 so as to bias proximal release sleeve 62. More particularly, in the present embodiment, proximal portion spring 64 is interposed between the spring engagement surface 18-7 of drive body 18 and proximal release sleeve 62 so as to bias proximal release sleeve 62 in proximal direction 38 toward proximal coupler latch position 40.

In turn, proximal release sleeve 62 is axially movable in distal direction 36 against the biasing force exerted by proximal portion spring 64 by an axial movement of proximal housing portion 60 from proximal coupler latch position 40 to first release position 52 (see, e.g., FIGS. 4 and 5) so as to operate release proximal latch member 20, i.e., having the pair of legs 46 (see FIG. 3), to facilitate removal of coupler device 16 from biopsy driver 12.

Referring to FIGS. 3 and 6, when proximal coupler portion 24 is assembled and coupled to drive body 18, proximal portion spring 64 is axially restrained, e.g., distally, by the engagement of distal end 64-2 of proximal portion spring 64 with intermediate lip 18-5 of drive body 18, and proximal retainer member 58 of proximal coupler portion 24 is axially restrained in proximal direction 38 by the engagement of annular retention lip 58-2 of proximal retainer member 58 with proximal lip 18-6 of drive body 18. Proximal release sleeve 62 and proximal portion spring 64 are radially surrounded by proximal housing portion 60, wherein proximal housing portion 60 is axially movable relative to drive body 18, and wherein proximal release sleeve 62 and proximal portion spring 64 are interposed between intermediate lip 18-5 of drive body 18 and proximal retainer member 58 of proximal coupler portion 24.

Referring again to FIGS. 1-5, in the present embodiment, distal coupler portion 26 includes distal housing portion 28 optionally having an external operator arm 70. External operator arm 70 is fixedly connected to, e.g., integral with, housing side wall 28-1 of distal housing portion 28. External operator arm 70 is an elongate member that extends in a cantilever manner in proximal direction 38 (in the orientation shown) from housing side wall 28-1. A length of external operator arm 70 may be selected such that a free end portion 70-1 of external operator arm 70 extends proximal to proximal housing portion 60 of proximal coupler portion 24 for ease of access by a user. Free end portion 70-1 is configured, e.g., in size and in shape, to facilitate push-pull operation of distal coupler portion 26. For example, free end portion 70-1 may include a flared end 70-2 forming a side-grip to aid the user in gripping during the pull operation, and flared end 70-2 may include end grip features 70-3, e.g., ridges or knurling, to aid in grip during a push operation.

Referring to FIGS. 3-6, in the present embodiment, distal coupler portion 26 also includes a distal release sleeve 72, a washer 74, a distal portion spring 76, a distal retainer member 78, and an intermediate retainer ring 80. Each of distal housing portion 28, distal release sleeve 72, washer 74, distal portion spring 76, distal retainer member 78, and an intermediate retainer ring 80 radially surrounds drive body 18. Washer 74 and distal portion spring 76 are axially interposed between distal release sleeve 72 and distal retainer member 78. Distal retainer member 78 is coupled, e.g., via a snap connection, to distal housing portion 28.

Distal housing portion 28 is a generally cylindrical structure having a housing side wall 28-1, a distal end region 28-2, a proximal end region 28-3. Distal end region 28-2 of distal housing portion 28 includes an annular bearing member 28-4. Proximal end region 28-3 of distal housing portion 28 includes a plurality of catch slots 28-5 (see FIGS. 4-6) that are annularly arranged around a periphery of housing side wall 28-1 to facilitate connection to a distal retainer member 78. Distal housing portion 28 radially surrounds distal release sleeve 72, washer 74, and distal portion spring 76.

Referring to FIG. 3, distal retainer member 78 is an annular ring member having a plurality of locking tabs 78-1 and a plurality of longitudinal slots 78-2. Referring to FIGS. 4 and 5, the plurality of locking tabs 78-1 are configured to engage the plurality of catch slots 28-5 at proximal end region 28-3 of distal housing portion 28 so as to connect distal retainer member 78 to distal housing portion 28.

Referring to FIGS. 3 and 6, intermediate retainer ring 80 includes an annular retention lip 80-1 and a plurality of indexing protrusions 80-2. Annular retention lip 80-1 extends radially inwardly toward longitudinal axis 30. Annular retention lip 80-1 is configured, e.g., in size and in shape, for connective engagement with intermediate annular recess 18-4 of drive body 18. The plurality of indexing protrusions 80-2 are located around and extend outwardly from an outer periphery 80-3 of intermediate retainer ring 80. Annular retention lip 80-1 of intermediate retainer ring 80 is configured, e.g., in size and in shape, to engage intermediate annular recess 18-4 of drive body 18 in a snap fit.

Referring to FIGS. 3, 6, 9 and 12, the plurality of indexing protrusions 80-2 of intermediate retainer ring 80 longitudinally engage the corresponding plurality of longitudinal slots 78-2 in distal retainer member 78, wherein distal retainer member 78 is axially slidably movable relative to intermediate retainer ring 80.

Referring to FIG. 3, intermediate retainer ring 80 may also include an interior detent member 80-4 at an interior periphery 80-5 of intermediate retainer ring 80. Interior detent member 80-4 of intermediate retainer ring 80 of distal coupler portion 26 is configured, e.g., in size and in shape, to selectively engage one of the plurality of indexing openings 60-5 of cylindrical extension 60-2 of proximal coupler portion 24 as distal coupler portion 26 is pivoted relative to proximal coupler portion 24, so as to rotationally index distal coupler portion 26 to one of multiple discrete intervals around longitudinal axis 30, as defined by the locations of the plurality of indexing openings 60-5 of cylindrical extension 60-2 of proximal coupler portion 24.

Referring again to FIGS. 7-12, distal release sleeve 72 is configured, e.g., in size and in shape, to be axially slidable along drive body 18 as well as to rotate in unison with drive body 18. In the present embodiment, distal housing portion 28 is operatively engaged, e.g., axially, with distal release sleeve 72 to axially slide distal release sleeve 72 of distal coupler portion 26 relative to drive body 18 in either of distal direction 36 or proximal direction 38 so as to operate distal latch member 22 to release drive body 18 from drive portion 14-1 (see also FIG. 2) of intraosseous device 14 to facilitate removal of intraosseous device 14 from coupler device 16. Distal release sleeve 72 is axially movable relative to proximally facing surface 18-10 of drive body 18.

Figure 14:
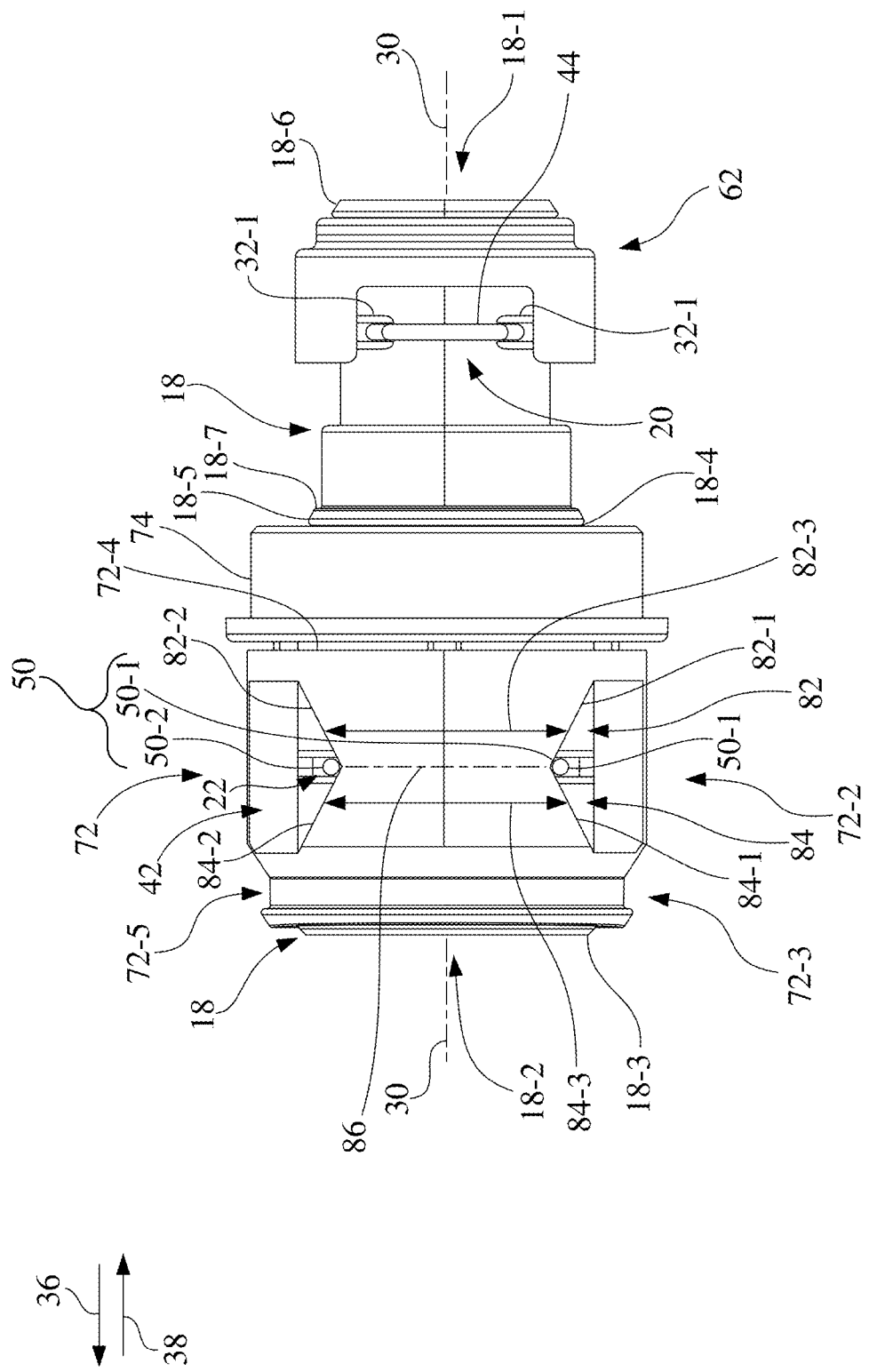
FIG. 14 is a side view of a portion of the coupler device of FIGS. 1-6, rotated 180 degrees from the orientation shown in FIG. 13, with the proximal and distal housing portions removed, and oriented to show a bidirectional wedge section of a distal release sleeve of the distal coupler portion positioned on the drive body of the coupler device, and with the distal release sleeve and a distal latch member in the latched position.

Referring to FIGS. 3 and 14, distal release sleeve 72 has a generally cylindrical shape having a side wall 72-1 with portions removed to define a bidirectional wedge section 72-2. Bidirectional wedge section 72-2 is configured, e.g., in size and in shape, to operate distal latch member 22. Distal release sleeve 72 also has a distal end portion 72-3 and a proximal end 72-4. Distal end portion 72-3 includes an annular bearing channel 72-5.

An interior of side wall 72-1 of distal release sleeve 72 includes a plurality of longitudinally extending channels 72-6. Distal release sleeve 72 is received over distal cylindrical portion 18-8 of drive body 18 and the plurality of longitudinally extending guide protrusion members 18-9 of drive body 18 are received in the plurality of longitudinally extending channels 72-6 of distal release sleeve 72. As such, distal release sleeve 72 is axially movable relative to drive body 18 and distal release sleeve 72 rotates in unison with drive body 18.

Annular bearing member 28-4 of distal housing portion 28 is configured, e.g., in size and in shape, to be received in annular bearing channel 72-5 of distal release sleeve 72 such that distal release sleeve 72 axially moves in unison with distal housing portion 28, and distal release sleeve 72 rotates in unison with drive body 18 in distal housing portion 28, e.g., distal housing portion 28 may be rotationally stationary when distal release sleeve 72 rotates in unison with drive body 18.

Distal coupler portion 26 and proximal coupler portion 24 may include detent features to provide tactile feedback to the user of the respective right-handed position and the left-handed position of distal housing portion 28. In the present embodiment, for example, interior detent member 80-4 of intermediate retainer ring 80 of distal coupler portion 26 may be selectively positioned in one of the plurality of indexing openings 60-5 of proximal housing portion 60 of proximal coupler portion 24 by rotating distal coupler portion 26 relative to proximal coupler portion 24 to selectively position interior detent member 80-4 of distal coupler portion 26 in one of the plurality of indexing openings 60-5 of proximal housing portion 60 of proximal coupler portion 24.

As such, distal housing portion 28 is pivotable (may be pivoted) around longitudinal axis 30 relative to distal release sleeve 72, e.g., 180 degrees, for selectively positioning external operator arm 70 on either of the diametrically opposed sides of longitudinal axis 30, i.e. on either of the opposite sides of driver housing 12-1 of biopsy driver 12, so as to accommodate either of right-handed use or left-handed use of distal coupler portion 26 in relation for biopsy driver 12.

Referring to FIGS. 3 and 6-9, distal coupler portion 26 is configured for bidirectional operation, such that when distal housing portion 28, e.g., having external operator arm 70, is moved in distal direction 36 toward intraosseous device 14, distal release sleeve 72 is moved from distal coupler latch position 42 to distal release position 54 such that bidirectional wedge section 72-2 (see also FIG. 14) of distal release sleeve 72 operates distal latch member 22 to facilitate removal of intraosseous device 14 (see FIG. 2) from distal drive receptacle 18-2 of drive body 18. Similarly, referring to FIGS. 3 and 10-12, distal coupler portion 26 is configured such that when distal housing portion 28, e.g., having external operator arm 70, is moved in proximal direction 38 toward biopsy driver 12, distal release sleeve 72 is moved from distal coupler latch position 42 to proximal release position 56 such that bidirectional wedge section 72-2 (see also FIG. 14) of distal release sleeve 72 operates distal latch member 22 to facilitate removal of intraosseous device 14 (see FIG. 2) from distal drive receptacle 18-2 of drive body 18.

Referring also to FIG. 14, bidirectional wedge section 72-2 of distal release sleeve 72 includes a first wedge member 82 and a second wedge member 84. First wedge member 82 is configured, e.g., in size and in shape, to apply an outwardly directed force to an interior surface 50-3 (see FIG. 3) of the pair of legs 50 of distal U-shaped member 22 to spread the pair of legs 50 of distal U-shaped member 22 apart to cause the pair of legs 50 of distal U-shaped member 22 to disengage from annular groove 14-5 (see FIG. 2) in drive portion 14-1 of intraosseous device 14 when distal release sleeve 72 is axially moved in distal direction 36 from distal coupler latch position 42 (see FIGS. 4-6) to distal release position 54 (see also FIGS. 7-9). Likewise, second wedge member 84 is configured, e.g., in size and in shape, to apply an outwardly directed force to interior surface 50-3 (see FIG. 3) of the pair of legs 50 of distal U-shaped member 22 to spread the pair of legs 50 of distal U-shaped member 22 apart to cause the pair of legs 50 of distal U-shaped member 22 to disengage from annular groove 14-5 (see FIG. 2) in drive portion 14-1 of intraosseous device 14 when distal release sleeve 72 is axially moved in proximal direction 38 from distal coupler latch position 42 to proximal release position 56 (see also FIGS. 10-12).

Referring again to FIG. 14, first wedge member 82 of distal release sleeve 72 is axially opposed to second wedge member 84 of distal release sleeve 72. First wedge member 82 joins second wedge member 84 at a plane of intersection 86, wherein when the pair of legs 50 (see also FIG. 3) of distal U-shaped member 22 is located at the plane of intersection 86, distal coupler portion 26 is in distal coupler latch position 42 (see FIGS. 4-6) and coupler device 16 is latched to drive portion 14-1 of intraosseous device 14 (see FIG. 2).

First wedge member 82 includes a first tapered surface 82-1 and a second tapered surface 82-2, wherein collectively, first tapered surface 82-1 and second tapered surface 82-2 tend to converge in distal direction 36 and, conversely, tend to diverge in proximal direction 38, in the orientation shown. First wedge member 82 is configured, e.g., in size and in shape, to apply an outwardly directed force to interior surface 50-3 (see FIG. 3) of the pair of legs 50 of distal U-shaped member 22 to spread the pair of legs 50 of distal U-shaped member 22 apart to cause the pair of legs 50 of proximal U-shaped member 20 to disengage from annular groove 14-5 (see FIG. 2) in drive portion 14-1 of intraosseous device 14 when distal release sleeve 72 of distal coupler portion 26 is axially moved in distal direction 36 from distal coupler latch position 42 (see FIGS. 4-6) to distal release position 54 (see FIGS. 7-9).

Accordingly, with reference to FIG. 14, as distal release sleeve 72 of distal coupler portion 26 is axially moved in distal direction 36, a distance 82-3 between first tapered surface 82-1 and a second tapered surface 82-2 increases at the points of intersection of first wedge member 82 with the pair of legs 50 (see FIG. 3) of distal latch member 22 so as to, in turn, increase the spacing between leg 50-1 and leg 50-2 of the pair of legs 50 of distal latch member 22. This increase of spacing between leg 50-1 and leg 50-2 then outwardly moves the pair of legs 50 in the pair of diametrically opposed slots 34-1 of distal slotted region 34 (see FIGS. 3 and 10) of drive body 18, which in turn radially withdraws the pair of legs 50 of distal latch member 22 from distal drive receptacle 18-2 so as to facilitate removal of intraosseous device 14 (see FIGS. 1 and 2) from distal coupler portion 26 of coupler device 16.

Second wedge member 84 includes a first tapered surface 84-1 and a second tapered surface 84-2, wherein collectively, first tapered surface 84-1 and second tapered surface 84-2 tend to converge in proximal direction 38 and, conversely, tend to diverge in distal direction 36, in the orientation shown. Second wedge member 84 is configured, e.g., in size and in shape, to apply an outwardly directed force to interior surface 50-3 (see FIG. 3) of the pair of legs 50 of distal U-shaped member 22 to spread the pair of legs 50 of distal U-shaped member 22 apart to cause the pair of legs 50 of proximal U-shaped member 20 to disengage from annular groove 14-5 (see FIG. 2) in drive portion 14-1 of intraosseous device 14 when distal release sleeve 72 of distal coupler portion 26 is axially moved in proximal direction 38 from distal coupler latch position 42 (see FIGS. 4-6) to distal release position 54 (see FIGS. 10-12).

Accordingly, with reference to FIG. 14, as distal release sleeve 72 of distal coupler portion 26 is axially moved in proximal direction 38, a distance 84-3 between first tapered surface 84-1 and a second tapered surface 84-2 increases at the points of intersection of second wedge member 84 with the pair of legs 50 (see FIG. 3) of distal latch member 22 so as to, in turn, increase the spacing between leg 50-1 and leg 50-2 of the pair of legs 50 of distal latch member 22. This increase of spacing between leg 50-1 and leg 50-2 then outwardly moves the pair of legs 50 in the pair of diametrically opposed slots 34-1 of distal slotted region 34 (see FIGS. 3 and 12) of drive body 18, which in turn radially withdraws the pair of legs 50 of distal latch member 22 from distal drive receptacle 18-2 so as to facilitate removal of intraosseous device 14 (see FIGS. 1 and 2) from distal coupler portion 26 of coupler device 16.

Distal portion spring 76 is interposed between distal release sleeve 72 and a combination of the plurality of indexing protrusions 80-2 of intermediate retainer ring 80 and distal retainer member 78. Distal portion spring 76 is configured, e.g., in size and in shape, to axially bias distal release sleeve 72 of distal coupler portion 26 to distal coupler latch position 42. More particularly, in the present embodiment, distal portion spring 76 is interposed between washer 74 and the combination of the plurality of indexing protrusions 80-2 of intermediate retainer ring 80 and distal retainer member 78. Both of proximally facing surface 18-10 of drive body 18 and distal release sleeve 72 of distal coupler portion 26 are located distal to distal portion spring 76.

Referring to FIGS. 6, 9, and 12, washer 74 is positioned to surround drive body 18. In the present embodiment, in section, washer 74 has a T-shaped profile. Washer 74 is interposed between proximally facing surface 18-10 of drive body 18 and distal portion spring 76. Washer 74 is interposed between distal release sleeve 72 of distal coupler portion 26 and distal portion spring 76.

With reference to FIG. 6, distal coupler portion 26 is configured such that when distal coupler portion 26 is in distal coupler latch position 42 (see also FIGS. 4-5), washer 74 is simultaneous in contact with both of proximally facing surface 18-10 of drive body 18 and distal release sleeve 72 of distal coupler portion 26.

With reference to FIG. 9, when distal coupler portion 26 is moved axially in distal direction 36 from distal coupler latch position 42 toward distal release position 54 by distal movement of distal housing portion 28 (e.g., a push action; see also FIGS. 7-8), the following events occur: distal release sleeve 72 of distal coupler portion 26 is moved toward distal release position 54 and distal release sleeve 72 separates from washer 74, washer 74 is in contact with proximally facing surface 18-10 of drive body 18 to prevent washer 74 from movement in distal direction 36, and distal portion spring 76 is compressed against washer 74 by movement of distal retainer member 78 in distal direction 36 along with distal housing portion 28 in distal direction 36.

Further, distal coupler portion 26 is configured such that when distal coupler portion 26 is released from movement in distal direction 36, distal portion spring 76 biases distal release sleeve 72 to distal coupler latch position 42 (see FIG. 6) via proximal movement of distal housing portion 28.

In addition, with reference to FIG. 12, distal coupler portion 26 is configured such that when distal coupler portion 26 is moved axially in proximal direction 38 from distal coupler latch position 42 (see FIGS. 4-6) toward proximal release position 56 by proximal movement of distal housing portion 28 (e.g., a pull action; see also FIGS. 10-11), the following events occur: distal release sleeve 72 of distal coupler portion 26 is moved toward proximal release position 56, washer 74 proximally separates from proximally facing surface 18-10 of drive body 18, and distal portion spring 76 is compressed against the plurality of indexing protrusions 80-2 of intermediate retainer ring 80 by movement of washer 74 in proximal direction 38 as distal retainer member 78 is moved in proximal direction 38 along with distal housing portion 28 in proximal direction 38.

Further, when distal coupler portion 26 (e.g., distal housing portion 28) is released from movement in proximal direction 38, then distal portion spring 76 biases distal release sleeve 72 to distal coupler latch position 42 (see FIG. 6).

While the embodiments of coupler device 16 depicted in FIGS. 1-14 includes both of distal coupler portion 26 and proximal coupler portion 24, it is to be recognized that, optionally, aspects of the invention associated with distal coupler portion 26 may be practiced alone, or in combination with a substitute for proximal coupler portion 24. Also, optionally, aspects of the invention associated with proximal coupler portion 24 may be practiced alone, or in combination with a substitute for distal coupler portion 26.

The following items also relate to the invention:

In one embodiment, the invention relates to a coupler device for interfacing between a driveshaft of a biopsy driver and a drive portion of an intraosseous device (a coupler device for a bone biopsy device). The coupler device may include a drive body, a distal latch member, and a distal coupler portion. The drive body may have a longitudinal axis and a distal drive receptacle. The drive body may be rotatable around the longitudinal axis. The (device may be configured such that the) distal drive receptacle may be configured to drivably couple to the drive portion of the intraosseous device. The distal latch member may be coupled to the drive body. The distal coupler portion may be coupled to the drive body and configured to operate the distal latch member. The distal coupler portion may be associated with the distal drive receptacle. The (device may be configured such that the) distal latch member may be configured to latch the drive body to the intraosseous device when the distal coupler portion is in a distal coupler latch position. The distal coupler portion may have a distal housing portion that is movable in either of a distal direction or a proximal direction. The (device may be configured such that the) distal coupler portion may be configured to have a distal release position and a proximal release position, wherein (the device may be configured such that the) distal housing portion may be configured to move in the distal direction to move the distal coupler portion to the distal release position to operate the distal latch member.

In any of the embodiments, the (device may be configured such that the) distal housing portion may be configured to move in the proximal direction to move the distal coupler portion to the proximal release position to operate the distal latch member.

In some embodiments, the coupler device may include a proximal latch member and a proximal coupler portion. The proximal latch member may be coupled to the drive body. The proximal coupler portion may be coupled to the drive body and may be configured to operate the proximal latch member. The (device may be configured such that the) proximal latch member may be configured to latch the drive body to the driveshaft of the biopsy driver when the proximal coupler portion is in a proximal coupler latch position. The (device may be configured such that the) proximal latch member may be configured to release the driveshaft of the biopsy driver when the proximal coupler portion is in a first release position. The drive body may have a proximal drive receptacle associated with the proximal coupler portion. The proximal drive receptacle may be configured to be coupled in driving engagement with the driveshaft of the biopsy driver.

In embodiments having the proximal coupler portion, the proximal coupler portion may include a proximal release sleeve axially slidable along the drive body. A proximal housing portion may radially surround the proximal release sleeve, wherein the (device may be configured such that the) proximal housing portion may be configured to engage the proximal release sleeve to axially slide the proximal release sleeve of the proximal coupler portion from the proximal coupler latch position to the first release position so as to operate the proximal latch member to release the drive body from the driveshaft of the biopsy driver to facilitate removal of the coupler device from the biopsy driver.

In embodiments having the proximal coupler portion, the drive body may have a proximal slotted region. The proximal slotted region may be configured to axially restrain the proximal latch member. The proximal latch member may be a proximal U-shaped member that has a pair of legs. The pair of legs of the proximal U-shaped member may be configured to engage the proximal slotted region in the driveshaft of the biopsy driver when the proximal coupler portion is in the proximal coupler latch position so as to latch the coupler device to the driveshaft of the biopsy driver. The proximal release sleeve may have a proximal wedge member configured to apply an outwardly directed force to an interior surface of the pair of legs of the proximal U-shaped member to spread the pair of legs of the proximal U-shaped member apart to cause the pair of legs of the proximal U-shaped member to disengage from the proximal slotted region in the driveshaft of the biopsy driver when the proximal release sleeve of the proximal coupler portion is axially moved from the proximal coupler latch position to the first release position.

In embodiments having a proximal release sleeve, the drive body may have a spring engagement surface, and the coupler device may further include a proximal portion spring interposed between the spring engagement surface of the drive body and the proximal release sleeve. The (device may be configured such that the) proximal portion spring may be configured to axially bias the proximal release sleeve of the proximal coupler portion to the proximal coupler latch position.

In any of the embodiments, the distal coupler portion may include a distal release sleeve axially slidable along the drive body. The (device may be configured such that the) distal housing portion may be configured to radially surround the distal release sleeve, wherein the distal housing portion may be operatively engaged with the distal release sleeve to axially slide the distal release sleeve of the distal coupler portion relative to the drive body to operate the distal latch member to release the drive body from the drive portion of the intraosseous device to facilitate removal of the intraosseous device from the coupler device. The (device may be configured such that the) distal coupler portion may be configured such that: when the distal housing portion is moved in the distal direction toward the intraosseous device, the distal release sleeve is moved from the distal coupler latch position to the distal release position to facilitate removal of the intraosseous device from the distal drive receptacle of the drive body, and when the distal housing portion is moved in the proximal direction toward the biopsy driver, the distal release sleeve is moved from the distal coupler latch position to the proximal release position to facilitate removal of the intraosseous device from the distal drive receptacle of the drive body.

In any of the embodiments, the drive body may have a distal slotted region. The distal slotted region may be configured to axially restrain the distal latch member. The distal latch member may be a distal U-shaped member that has a pair of legs. The (device may be configured such that the) pair of legs of the distal U-shaped member may be configured to engage a groove in the drive portion of the intraosseous device when the distal coupler portion is in the distal coupler latch position so as to latch the coupler device to the drive portion of the intraosseous device. The distal release sleeve may include a first wedge member and a second wedge member. The (device may be configured such that the) first wedge member may be configured to apply an outwardly directed force to an interior surface of the pair of legs of the distal U-shaped member to spread the pair of legs of the distal U-shaped member apart to cause the pair of legs of the distal U-shaped member to disengage from the groove in the drive portion of the intraosseous device when the distal release sleeve is axially moved in the distal direction from the distal coupler latch position to the distal release position. The (device may be configured such that the) second wedge member may be configured to apply an outwardly directed force to the interior surface of the pair of legs of the distal U-shaped member to spread the pair of legs of the distal U-shaped member apart to cause the pair of legs of the distal U-shaped member to disengage from the groove in the drive portion of the intraosseous device when the distal release sleeve is axially moved in the proximal direction from the distal coupler latch position to the proximal release position.

In the embodiment of the preceding paragraph, the first wedge member of the distal release sleeve may be axially opposed to the second wedge member of the distal release sleeve, the first wedge member may join the second wedge member at a plane of intersection, and (the device may be configured such that the first wedge member of the distal release sleeve may be) configured such that when the pair of legs of the distal U-shaped member is located at the plane of intersection, the distal coupler portion is in the distal coupler latch position and the coupler device is latched to the drive portion of the intraosseous device.

In any of the embodiments, the distal coupler portion may further include a distal retainer member and a distal portion spring. The distal retainer member may be coupled to the distal housing portion. The distal portion spring may be interposed between the distal retainer member and the distal release sleeve. The (device may be configured such that the) distal portion spring may be configured to axially bias the distal release sleeve of the distal coupler portion to the distal coupler latch position.

In any of the embodiments, the drive body may have a proximally facing surface, and both of the proximally facing surface of the drive body and the distal release sleeve of the distal coupler portion may be located distal to the distal portion spring. The (device may be configured such that the) distal release sleeve may be configured to be axially movable relative to the proximally facing surface of the drive body. The distal coupler portion may include a washer positioned to surround the drive body, and configured wherein the washer is interposed between the proximally facing surface of the drive body and the distal portion spring, and wherein the washer is interposed between the distal release sleeve of the distal coupler portion and the distal portion spring.

In the embodiment of the preceding paragraph, the (device may be configured such that the) distal coupler portion may be configured such that when the distal coupler portion is in the distal coupler latch position, the washer is in simultaneous contact with both of the proximally facing surface of the drive body and the distal release sleeve of the distal coupler portion.

In embodiments having the washer, the (device may be configured such that the) distal coupler portion may be configured such that when the distal coupler portion is moved axially in the distal direction from the distal coupler latch position toward the distal release position by distal movement of the distal housing portion, the distal release sleeve of the distal coupler portion is moved toward the distal release position and the distal release sleeve separates from the washer, the washer is in contact with the proximally facing surface of the drive body to prevent the washer from movement in the distal direction, and the distal portion spring is compressed against the washer by movement of the distal retainer member in the distal direction.

In the embodiment of the preceding paragraph, the (device may be configured such that the) distal coupler portion may be configured such that when the distal coupler portion is released from movement in the distal direction, the distal portion spring biases the distal release sleeve to the distal coupler latch position.

In embodiments having the washer, the (device may be configured such that the) distal coupler portion may be configured such that when the distal coupler portion is moved axially in the proximal direction from the distal coupler latch position toward the proximal release position by proximal movement of the distal housing portion, the distal release sleeve of the distal coupler portion is moved toward the proximal release position, the washer proximally separates from the proximally facing surface of the drive body, and the distal portion spring is compressed by movement of the washer in the proximal direction.

In the embodiment of the preceding paragraph, the (device may be configured such that the) distal coupler portion may be configured such that when the distal coupler portion is released from movement in the proximal direction, the distal portion spring biases the distal release sleeve to the distal coupler latch position.

In some embodiments, the (device may be configured such that the) distal coupler portion may be configured such that a distal end of the distal coupler portion is axially movable in the distal direction beyond a distal end of the drive body.

In some embodiments, the drive body may include a distal cylindrical portion that may have a plurality of longitudinally extending guide protrusion members. The distal release sleeve may have a plurality of longitudinally extending channels. The (device may be configured such that the) distal release sleeve may be received over the distal cylindrical portion and the plurality of longitudinally extending guide protrusion members of the drive body may be received in the plurality of longitudinally extending channels of the distal release sleeve, wherein the distal release sleeve is axially movable relative to the drive body and wherein the distal release sleeve rotates in unison with the drive body.

In some embodiments, the distal release sleeve may have an annular bearing channel, the (device may be configured such that the) distal release sleeve configured to rotate in unison with the drive body; and the (device may be configured such that the) distal housing portion may have an annular bearing member configured to be received in the annular bearing channel of the distal release sleeve such that the distal release sleeve axially moves in unison with the distal housing portion, and the distal housing portion may be rotationally stationary when the distal release sleeve rotates in unison with the drive body.

In any of the preceding embodiments, an external operator arm may be coupled to the distal housing portion, wherein the (device may be configured such that the) distal coupler portion may be configured to pivot relative to the proximal coupler portion around the longitudinal axis for selectively positioning the external operator arm on diametrically opposed sides of the longitudinal axis to accommodate either of right-handed use or left-handed use of the distal coupler portion.

In one embodiment, the invention relates to a biopsy system. The biopsy system may include a biopsy driver that has a driveshaft, an intraosseous device that has a drive portion, and a coupler device for interfacing between the driveshaft of the biopsy driver and the drive portion of the intraosseous device. The coupler device may be configured according to any of the previous embodiments of any of the preceding par.

As used herein, "substantially," "generally," "slightly" and other words of degree are relative modifiers intended to indicate permissible variation from the characteristic so modified. It is not intended to be limited to the absolute value or characteristic which it modifies but rather possessing more of the physical or functional characteristic than its opposite, and approaching or approximating such a physical or functional characteristic.

Also, as used herein, the term "coupled", and its derivatives, is intended to embrace any operationally functional connection, i.e., a direct connection or an indirect connection.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A coupler device for interfacing between a driveshaft of a biopsy driver and a drive portion of an intraosseous device, comprising:
a drive body having a longitudinal axis and a distal drive receptacle, the drive body being rotatable around the longitudinal axis, the distal drive receptacle is configured to drivably couple to the drive portion of the intraosseous device;
a distal latch member coupled to the drive body; and
a distal coupler portion coupled to the drive body and configured to operate the distal latch member, the distal coupler portion being associated with the distal drive receptacle, the distal latch member configured to latch the drive body to the intraosseous device when the distal coupler portion is in a distal coupler latch position, the distal coupler portion having a distal housing portion that is movable in either of a distal direction or a proximal direction,
the distal coupler portion configured to have a distal release position and a proximal release position, wherein the distal housing portion is configured to move in the distal direction to move the distal coupler portion to the distal release position to operate the distal latch member.

2. The coupler device according to claim 1, wherein the distal housing portion is configured to move in the proximal direction to move the distal coupler portion to the proximal release position to operate the distal latch member.

3. The coupler device according to claim 1, comprising:
a proximal latch member coupled to the drive body; and
a proximal coupler portion coupled to the drive body and configured to operate the proximal latch member, the proximal latch member configured to latch the drive body to the driveshaft of the biopsy driver when the proximal coupler portion is in a proximal coupler latch position, and the proximal latch member configured to release the driveshaft of the biopsy driver when the proximal coupler portion is in a first release position,
wherein the drive body has a proximal drive receptacle associated with the proximal coupler portion, the proximal drive receptacle configured to be coupled in driving engagement with the driveshaft of the biopsy driver.

4. The coupler device according to claim 3, the proximal coupler portion comprising:
a proximal release sleeve axially slidable along the drive body; and
a proximal housing portion that radially surrounds the proximal release sleeve, wherein:
the proximal housing portion is configured to engage the proximal release sleeve to axially slide the proximal release sleeve of the proximal coupler portion from the proximal coupler latch position to the first release position so as to operate the proximal latch member to release the drive body from the driveshaft of the biopsy driver to facilitate removal of the coupler device from the biopsy driver.

5. The coupler device according to claim 4, wherein:
the drive body has a proximal slotted region, the proximal slotted region configured to axially restrain the proximal latch member;
the proximal latch member is a proximal U-shaped member having a pair of legs, the pair of legs of the proximal U-shaped member configured to engage the proximal slotted region in the driveshaft of the biopsy driver when the proximal coupler portion is in the proximal coupler latch position so as to latch the coupler device to the driveshaft of the biopsy driver; and
the proximal release sleeve has a proximal wedge member configured to apply an outwardly directed force to an interior surface of the pair of legs of the proximal U-shaped member to spread the pair of legs of the proximal U-shaped member apart to cause the pair of legs of the proximal U-shaped member to disengage from the proximal slotted region in the driveshaft of the biopsy driver when the proximal release sleeve of the proximal coupler portion is axially moved from the proximal coupler latch position to the first release position.

6. The coupler device according to claim 5, wherein the drive body has a spring engagement surface, and the coupler device further comprising a proximal portion spring interposed between the spring engagement surface of the drive body and the proximal release sleeve, the proximal portion spring configured to axially bias the proximal release sleeve of the proximal coupler portion to the proximal coupler latch position.

7. The coupler device according to claim 3, comprising an external operator arm coupled to the distal housing portion, wherein the distal coupler portion is configured to pivot relative to the proximal coupler portion around the longitudinal axis for selectively positioning the external operator arm on diametrically opposed sides of the longitudinal axis to accommodate either of right-handed use or left-handed use of the distal coupler portion.

8. The coupler device according to claim 1, the distal coupler portion comprising:
a distal release sleeve axially slidable along the drive body; and
the distal housing portion is configured to radially surround the distal release sleeve, wherein:
the distal housing portion is operatively engaged with the distal release sleeve to axially slide the distal release sleeve of the distal coupler portion relative to the drive body to operate the distal latch member to release the drive body from the drive portion of the intraosseous device to facilitate removal of the intraosseous device from the coupler device, the distal coupler portion configured such that:
when the distal housing portion is moved in the distal direction toward the intraosseous device, the distal release sleeve is moved from the distal coupler latch position to the distal release position to facilitate removal of the intraosseous device from the distal drive receptacle of the drive body, and when the distal housing portion is moved in the proximal direction toward the biopsy driver, the distal release sleeve is moved from the distal coupler latch position to the proximal release position to facilitate removal of the intraosseous device from the distal drive receptacle of the drive body.

9. The coupler device according to claim 8, wherein:
the drive body has a distal slotted region, the distal slotted region configured to axially restrain the distal latch member;
the distal latch member is a distal U-shaped member having a pair of legs, the pair of legs of the distal U-shaped member configured to engage a groove in the drive portion of the intraosseous device when the distal coupler portion is in the distal coupler latch position so as to latch the coupler device to the drive portion of the intraosseous device; and
the distal release sleeve includes a first wedge member and a second wedge member, wherein:
the first wedge member is configured to apply an outwardly directed force to an interior surface of the pair of legs of the distal U-shaped member to spread the pair of legs of the distal U-shaped member apart to cause the pair of legs of the distal U-shaped member to disengage from the groove in the drive portion of the intraosseous device when the distal release sleeve is axially moved in the distal direction from the distal coupler latch position to the distal release position, and
the second wedge member is configured to apply an outwardly directed force to the interior surface of the pair of legs of the distal U-shaped member to spread the pair of legs of the distal U-shaped member apart to cause the pair of legs of the distal U-shaped member to disengage from the groove in the drive portion of the intraosseous device when the distal release sleeve is axially moved in the proximal direction from the distal coupler latch position to the proximal release position.

10. The coupler device according to claim 9, wherein the first wedge member of the distal release sleeve is axially opposed to the second wedge member of the distal release sleeve, and wherein the first wedge member joins the second wedge member at a plane of intersection, wherein when the pair of legs of the distal U-shaped member is located at the plane of intersection, the distal coupler portion is in the distal coupler latch position and the coupler device is latched to the drive portion of the intraosseous device.

11. The coupler device according to claim 8, the distal coupler portion further comprising:
a distal retainer member coupled to the distal housing portion; and
a distal portion spring interposed between the distal retainer member and the distal release sleeve, the distal portion spring configured to axially bias the distal release sleeve of the distal coupler portion to the distal coupler latch position.

12. The coupler device according to claim 11, wherein:
the drive body has a proximally facing surface, and both of the proximally facing surface of the drive body and the distal release sleeve of the distal coupler portion are located distal to the distal portion spring, the distal release sleeve configured to be axially movable relative to the proximally facing surface of the drive body, and
the distal coupler portion further comprises a washer positioned to surround the drive body, wherein the washer is interposed between the proximally facing surface of the drive body and the distal portion spring, and wherein the washer is interposed between the distal release sleeve of the distal coupler portion and the distal portion spring.

13. The coupler device according to claim 12, wherein the distal coupler portion is configured such that when the distal coupler portion is in the distal coupler latch position, the washer is in simultaneous contact with both of the proximally facing surface of the drive body and the distal release sleeve of the distal coupler portion.

14. The coupler device according to claim 12, wherein the distal coupler portion is configured such that when the distal coupler portion is moved axially in the distal direction from the distal coupler latch position toward the distal release position by distal movement of the distal housing portion,
the distal release sleeve of the distal coupler portion is moved toward the distal release position and the distal release sleeve separates from the washer,
the washer is in contact with the proximally facing surface of the drive body to prevent the washer from movement in the distal direction, and
the distal portion spring is compressed against the washer by movement of the distal retainer member in the distal direction.

15. The coupler device according to claim 14, the distal coupler portion is configured such that when the distal coupler portion is released from movement in the distal direction, the distal portion spring biases the distal release sleeve to the distal coupler latch position.

16. The coupler device according to claim 12, wherein the distal coupler portion is configured such that when the distal coupler portion is moved axially in the proximal direction from the distal coupler latch position toward the proximal release position by proximal movement of the distal housing portion,
the distal release sleeve of the distal coupler portion is moved toward the proximal release position,
the washer proximally separates from the proximally facing surface of the drive body, and
the distal portion spring is compressed by movement of the washer in the proximal direction.

17. The coupler device according to claim 16, the distal coupler portion is configured such that when the distal coupler portion is released from movement in the proximal direction, the distal portion spring biases the distal release sleeve to the distal coupler latch position.

18. The coupler device according to claim 8, wherein the distal coupler portion is configured such that a distal end of the distal coupler portion is axially movable in the distal direction beyond a distal end of the drive body.

19. The coupler device according to claim 8, wherein:
the drive body includes a distal cylindrical portion having a plurality of longitudinally extending guide protrusion members, and
the distal release sleeve has a plurality of longitudinally extending channels,
wherein the distal release sleeve is received over the distal cylindrical portion and the plurality of longitudinally extending guide protrusion members of the drive body are received in the plurality of longitudinally extending channels of the distal release sleeve, wherein the distal release sleeve is axially movable relative to the drive body and wherein the distal release sleeve rotates in unison with the drive body.

20. The coupler device according to claim 8, wherein:
the distal release sleeve has an annular bearing channel, the distal release sleeve configured to rotate in unison with the drive body; and the distal housing portion has an annular bearing member configured to be received in the annular bearing channel of the distal release sleeve such that the distal release sleeve axially moves in unison with the distal housing portion, and the distal housing portion is rotationally stationary when the distal release sleeve rotates in unison with the drive body.

21. A biopsy system, comprising:
a biopsy driver having a driveshaft;
an intraosseous device having a drive portion; and
a coupler device for interfacing between the driveshaft of the biopsy driver and the drive portion of the intraosseous device, the coupler device being configured according to claim 1.

\* \* \* \* \*